US012669514B2

(12) United States Patent
Yan et al.

(10) Patent No.: US 12,669,514 B2
(45) Date of Patent: Jun. 30, 2026

(54) MASS TAGS FOR LIPID ANALYSES

(71) Applicant: THE TEXAS A&M UNIVERSITY SYSTEM, College Station, TX (US)

(72) Inventors: Xin Yan, College Station, TX (US); Tingyuan Yang, College Station, TX (US); Shuli Tang, College Station, TX (US); Xi Chen, College Station, TX (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 481 days.

(21) Appl. No.: 18/554,064

(22) PCT Filed: Apr. 6, 2022

(86) PCT No.: PCT/US2022/023580
§ 371 (c)(1),
(2) Date: Oct. 5, 2023

(87) PCT Pub. No.: WO2022/216767
PCT Pub. Date: Oct. 13, 2022

(65) Prior Publication Data
US 2024/0230687 A1 Jul. 11, 2024

Related U.S. Application Data

(60) Provisional application No. 63/171,846, filed on Apr. 7, 2021.

(51) Int. Cl.
*G01N 33/92* (2006.01)
*C07D 213/73* (2006.01)
*C07D 401/12* (2006.01)
*G01N 33/58* (2006.01)

(52) U.S. Cl.
CPC ........... *G01N 33/92* (2013.01); *C07D 213/73* (2013.01); *C07D 401/12* (2013.01); *G01N 33/58* (2013.01); *G01N 2560/00* (2013.01)

(58) Field of Classification Search
None
See application file for complete search history.

(56) References Cited

U.S. PATENT DOCUMENTS 8,501,498 B2 * 8/2013 Yan .................... C07D 295/185 436/544
2008/0241074 A1 10/2008 Bornhop et al.
2010/0178710 A1 7/2010 Hamon et al.
2010/0222331 A1 9/2010 Engelhardt et al.
(Continued)

OTHER PUBLICATIONS

PCT Search Report and Written Opinion prepared for PCT Application No. PCT/US2022/023580, completed Jun. 6, 2022.
(Continued)

*Primary Examiner* — Henry H Nguyen
(74) *Attorney, Agent, or Firm* — Barnes & Thornburg LLP

(57) ABSTRACT

The present disclosure provides compositions comprising novel mass tags. The disclosure also provides methods utilizing mass tags, including methods of quantifying one or more individual lipids from a composition of lipids, methods of identifying a double bond position of an individual lipid, methods of identifying a biological correlation of an individual lipid, and methods of preparing a lipid derivative.

19 Claims, 18 Drawing Sheets

(56) References Cited

U.S. PATENT DOCUMENTS

| | | | | |
|---|---|---|---|---|
| 2012/0196378 | A1 | 8/2012 | Purkayastha et al. | |
| 2012/0283137 | A1* | 11/2012 | Baumann ............. | C07D 401/12<br>546/208 |
| 2016/0349277 | A1 | 12/2016 | Stubiger et al. | |

OTHER PUBLICATIONS

He, Wei, et al. "Nonbenzamidine Compounds as Selective Factor Xa Inhibitors," 2000, Bioorganic & Medicinal Chemistry Letters, No. 10, pp. 1737-1739.

PubChem-S1D-329747139, Modify Date: Mar. 14, 2018 (Mar. 14, 2018), p. 2, figure, this is a purchasable chemical.

PubChem-S1D-329747561, Modify Date: Mar. 14, 2018 (Mar. 14, 2018), p. 2, figure, this is a purchasable chemical.

PubChem-S1D-329768165, Modify Dale: Mar. 14, 2018 (Mar. 14, 2018), p. 2, figure, this is a purchasable chemical.

PubChem-S1D-329756080, Modify Date: Mar. 14, 2018 (Mar. 14, 2018), p. 2, figure, this is a purchasable chemical.

* cited by examiner

FIG. 2D
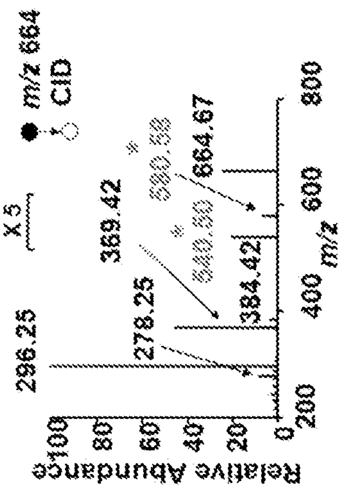
FIG. 2E
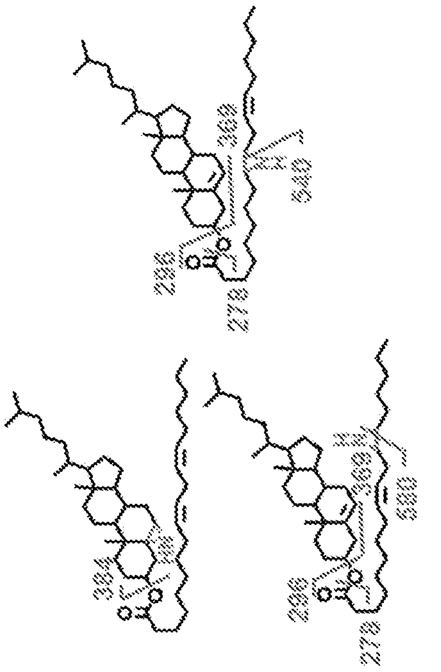
FIGS. 2D-2E

FIG. 5A
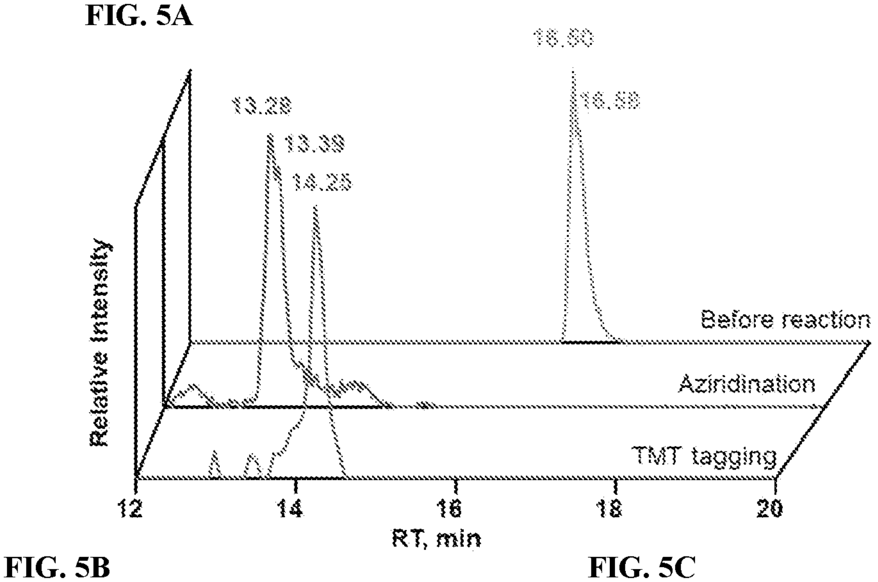
FIG. 5B
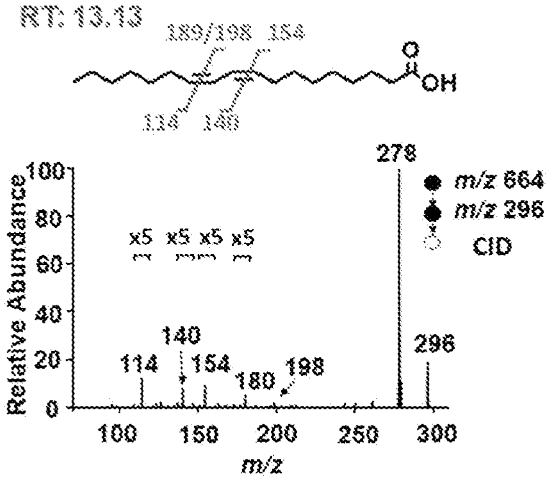
FIG. 5C
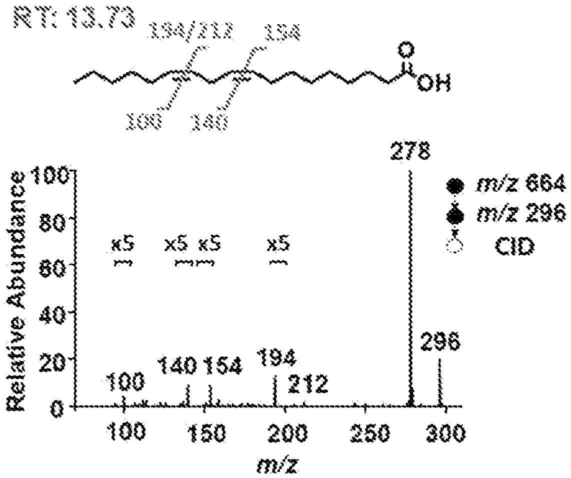
FIG. 5D
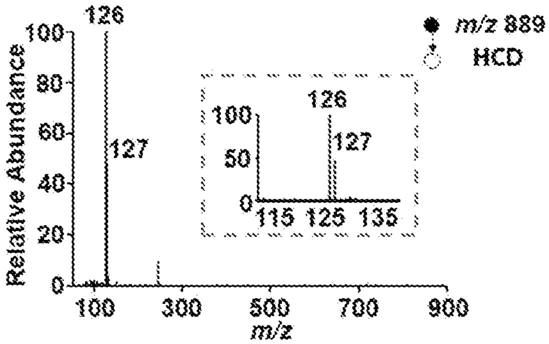
FIG. 5E
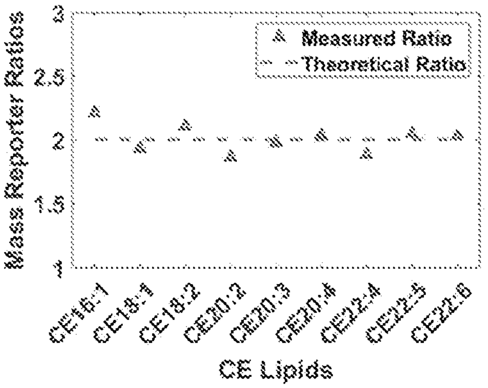
FIGS. 5A-5E

MASS TAGS FOR LIPID ANALYSES

CROSS-REFERENCE TO RELATED APPLICATIONS

This application is a national stage entry under 35 USC § 371(b) of PCT International Application No. PCT/US2022/023580, filed Apr. 6, 2022, which claims the benefit under 35 USC § 119(e) of U.S. Provisional Application Ser. No. 63/171,846, filed on Apr. 7, 2021, the entire disclosures of which is are incorporated herein by reference.

BACKGROUND AND SUMMARY OF THE INVENTION

Unsaturated lipids represent a dominant portion of total lipids in mammalian cells. Importantly, unsaturated lipids play essential roles in biological systems, acting as building blocks of cell membranes, mediators for signaling, and key molecules for energy storage. The concentrations of unsaturated lipids are tightly controlled in regulating a wide range of biological activities and changes in the levels of lipid species can occur after physiological perturbation. As a result, knowing the concentrations of individual lipids is essential to elucidate their roles in physiological processes including markers for diseases.

Furthermore, lipids often exist as mixtures of isomers, varying in lipid head groups, fatty acyl chain lengths, double bond positions and configurations. Small variations in structure result in unique roles in lipid homeostasis and pathology. For instance, a strong correlation has been recognized between double bond positional isomers and the onset/progression of breast cancer, while a change in lipid double bond position is a tissue marker for diagnosing human lung cancer. These results highlight the importance of lipid quantification at the isomer level in disease diagnosis and understanding of pathologies.

Mass spectrometry (MS) is a vital tool for lipid analysis due to its high sensitivity and high specificity. Using tandem MS, some structural information of lipids can be elucidated, such as lipid head group, fatty acyl chain lengths. However, due to high stability of C═C bonds, common fragmentation methods (e.g., collision-induced dissociation (CID) and higher-energy C-trap dissociation (HCD)) are not able to break the C═C bonds. Thus, structure characterization is challenging in C═C bond position identification. Although advances such as ultraviolet photodissociation (UVPD), ozone-induced dissociation, Paternò-Büchi(P-B) reaction, epoxidation have been attempted, these methodologies have resulted in little improvement in lipid ionization efficiency. In particular, means neutral and nonpolar lipids that usually are not easily ionized in the solution cannot be detected by MS, let alone be identified and quantified.

The use of lipid internal standards (ISs) can be attempted in MS-based lipid quantification via addition of synthetic or stable isotope-labeled lipids to remove the influence of matrix effects from different samples on the ionization efficiencies. However, proper lipid quantification has proven to be difficult since lipids are so structurally diverse. Further, it is impractical to prepare multiple labeled ISs for each lipid existing in a biological sample and it is unrealistic to prepare and add ISs of optimal concentrations that match those of the target molecules. This method also suffers with regards to sample throughput, i.e., one sample per experimental run. Therefore, there exists a need for new compositions and methods for quantification of individual lipids.

Accordingly, the present disclosure provides compositions and associated methods to address these problems. For instance, using an aziridination reaction scheme, a three-membered ring is formed for ease of identifying C═C bond positions in individual lipids. Furthermore, molecules are more likely to be ionized due to the existence of nitrogen which makes it possible for analyzing nonpolar lipids.

In addition, novel mass tags are employed for lipid relative quantification, utilizing the nitrogen atom in the aziridine functional group. After tagging, the same lipid from different sample pools shares equal m/z, while m/z of mass reporters are distinct. According to mass reporter ratios obtained in HCD, the relative concentrations of lipids can be ascertained.

The compositions and methods provided herein provide several benefits compared to the state of the art. In particular, the present disclosure provides a general and efficient approach for at least three different functions: (i) quantification of unsaturated lipids; (ii) determination of lipid double bond positional isomers, and (iii) improvement of lipid ionization efficiency. The methods disclosed herein can be utilized without the requirement of adding internal standards and can also overcome the matrix effects from different samples. Furthermore, the method of quantifying individual lipids and identifying a double bond position of individual lipids from a composition of lipids can be performed simultaneously, thus providing a precise and efficient system compared to the art.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2A-2E show methods for locating C═C bond positions in ethyl oleate lipid and CE 18:2 lipid. FIG. 2A shows a synthesis route of ethyl oleate lipid aziridine.

FIG. 2B shows full mass spectrum of reaction mixture after aziridination of ethyl oleate. FIG. 2C shows CID tandem mass spectrum of ethyl oleate aziridine. Diagnostic ions are labeled with stars. FIG. 2D shows CID tandem mass spectrum of mono-aziridination product. Diagnostic ions are labeled with stars. FIG. 2E shows structures and fragmentation pathways of mono-aziridination products.

FIG. 3A: FA 16:1 (9Z); FIG. 3B: FA 18:1 (9Z); FIG. 3C: PC 16:0/18:1 (9Z); FIG. 3D: PC 16:0/18:2 (9Z,12Z); FIG. 3E: PA 16:0/18:1 (9Z); FIG. 3F: PE 16:0/18:1 (9Z); FIG. 3G: CE 18:1 (9Z); FIG. 3H: TG 18:1 (9Z)/18:1 (9Z)/18:1 (9Z); FIG. 3I: TG 18:2 (9Z, 12Z)/18:2 (9Z, 12Z)/18:2 (9Z, 12Z). Diagnostic ions are labeled in red color and indicated with stars.

FIG. 4A shows a synthesis route of tagged ethyl oleate with different isobaric labeled tags; concentration ratio of ethyl oleate from different samples is 1:2. FIG. 4B shows HCD tandem mass spectrum of tagged lipid, and mass reporter peaks at m/z 126 and 127 are detected. Mass reporter ratio indicates the concentration ratio of starting lipids. FIG. 4C shows the linear correlation between measured relative abundance of reporter ions (126:127) and different molar ratios of tag-labeled ethyl oleate.

FIG. 5A shows extracted ion chromatogram of CE 18:2 lipid before reaction, after aziridination and after mass tagging. FIG. 5B shows CID tandem mass spectrum of CE 18:2 lipid aziridine at RT 13.13 min. FIG. 5C shows CID tandem mass spectrum of CE 18:2 lipid aziridine at RT 13.73 min. FIG. 5D shows HCD tandem mass spectrum of mass tagged CE 18:2 lipid and mass reporters at m/z 126 and 127 were shown.

FIG. 5E shows show mass reported ratios achieved from different tagged CE lipids (triangles) and a dashed line presenting the theoretical mass reporter ratios.

DETAILED DESCRIPTION

Figure 1A:
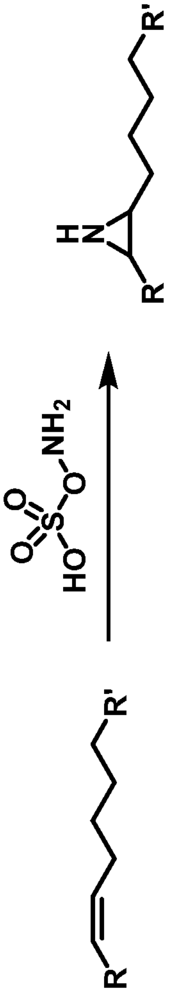
FIGS. 1A-1B show an exemplary aziridination reaction of unsaturated lipids for lipid analysis.
Figure 1B:
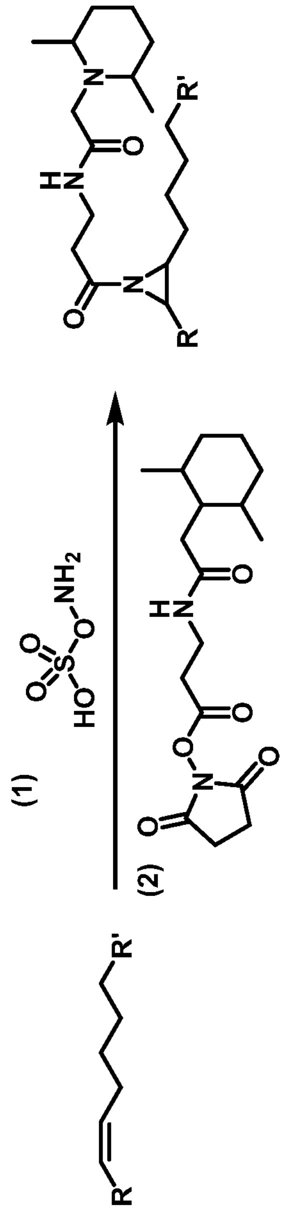

Various embodiments of the invention are described herein as follows. In an illustrative aspect, a composition comprising a mass tag is provided, wherein the mass tag has a particular structure. According to the present disclosure, a mass tag is intended to react with an unsaturated lipid, for instance by undergoing an aziridination reaction or a Paternò-Büchi reaction.

In some embodiments, the mass tag has a structure selected from the group consisting of a member of a Group I mass tag, a Group II mass tag, and a Group III mass tag.

Group I mass tags include but are not limited to the following structures. Without being bound by any theory, it is believed that Group I mass tags undergo an aziridination reaction with unsaturated lipids. The Group I mass tags can be utilized according to the various methods described herein.

Group I Mass Tags

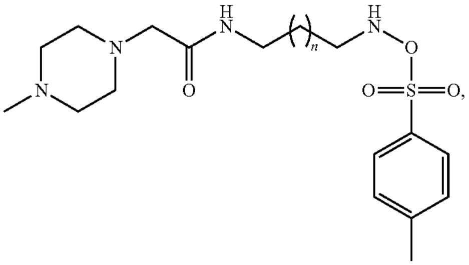

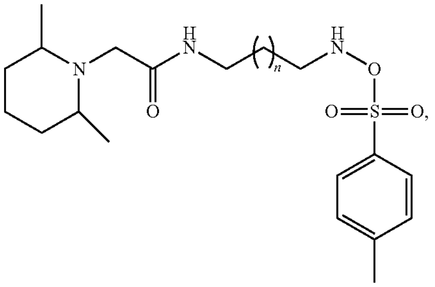

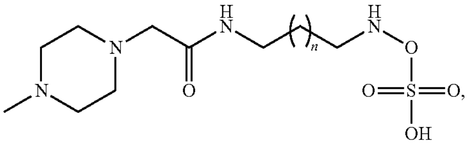

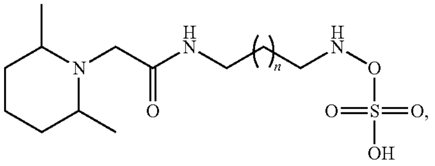

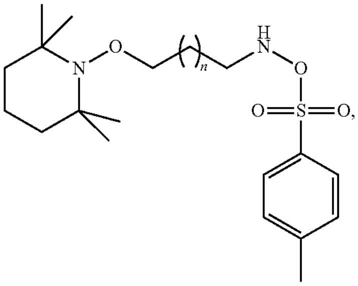

and

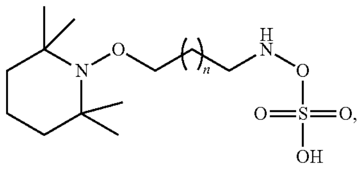

wherein n is between 0 and 10.

Group II mass tags include but are not limited to the following structures. Without being bound by any theory, it is believed that Group II mass tags undergo an aziridination reaction with unsaturated lipids. The Group II mass tags can be utilized according to the various methods described herein.

Group II Mass Tags

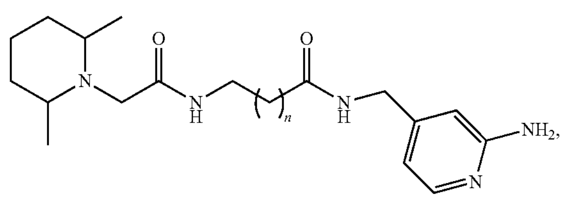

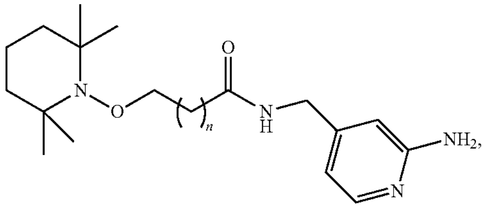

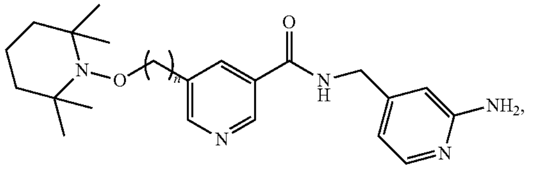

and

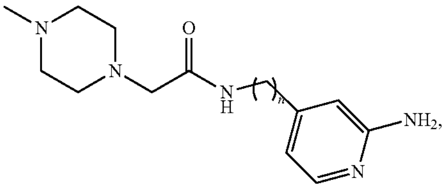

wherein n is between 0 and 10.

Group III mass tags include but are not limited to the following structures. Without being bound by any theory, it is believed that Group III mass tags undergo a Paternò-Büchi reaction with unsaturated lipids. The Group III mass tags can be utilized according to the various methods described herein.

Group III Mass Tags

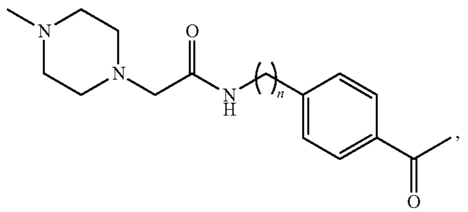

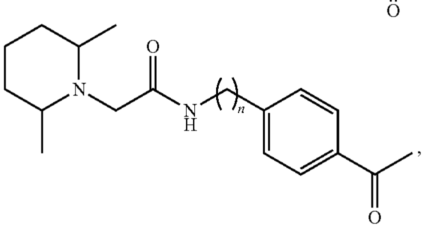

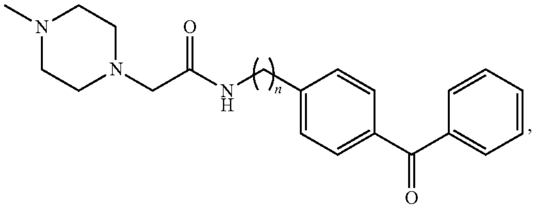

-continued

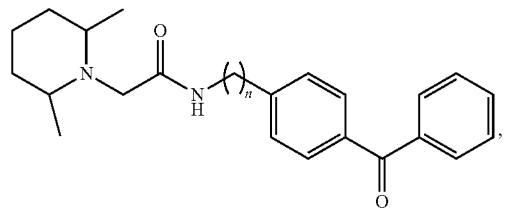

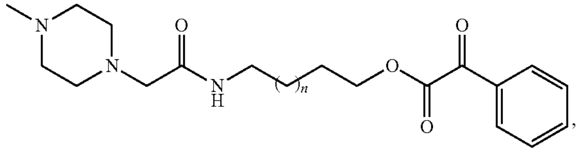

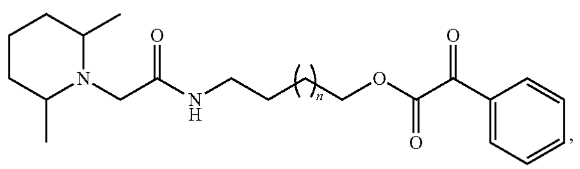

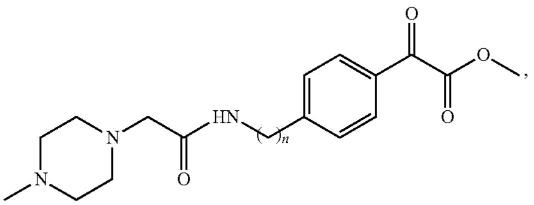

and

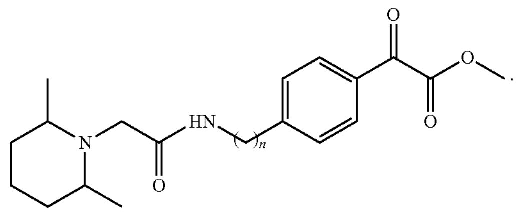

wherein n is between 0 and 10.

In an embodiment, the mass tag has a structure of

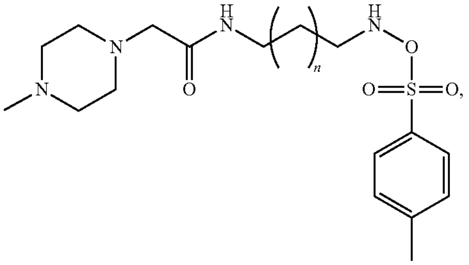

wherein n is between 0 and 10.

In an embodiment, the mass tag has a structure of

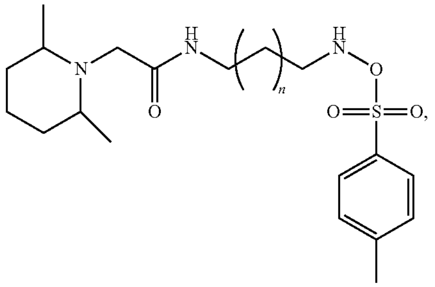

wherein n is between 0 and 10.

In an embodiment, the mass tag has a structure of

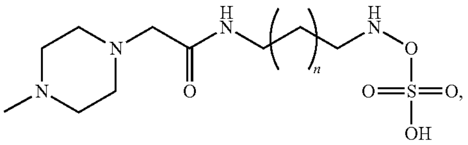

wherein n is between 0 and 10.

In an embodiment, the mass tag has a structure of

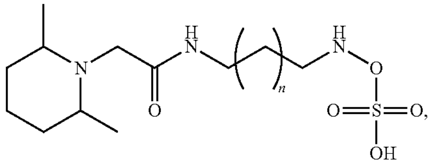

wherein n is between 0 and 10.

In an embodiment, the mass tag has a structure of

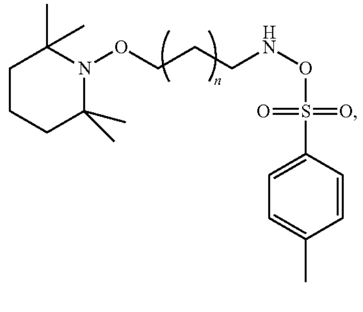

wherein n is between 0 and 10.

In an embodiment, the mass tag has a structure of

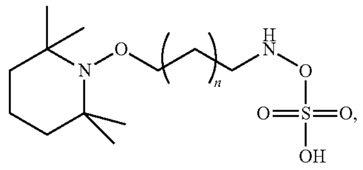

wherein n is between 0 and 10.

In an embodiment, the mass tag has a structure of

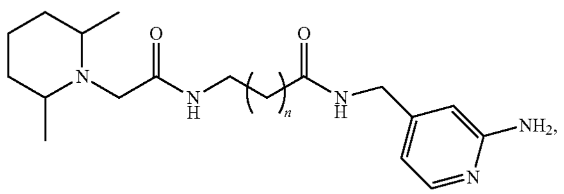

wherein n is between 0 and 10.

In an embodiment, the mass tag has a structure of

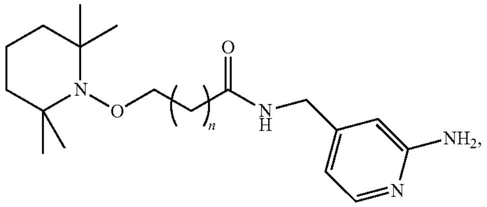

wherein n is between 0 and 10.

In an embodiment, the mass tag has a structure of

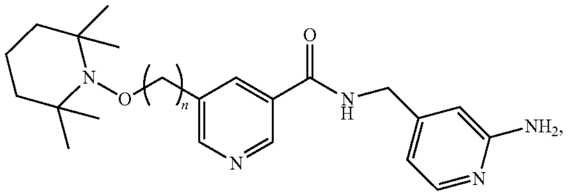

wherein n is between 0 and 10.

In an embodiment, the mass tag has a structure of

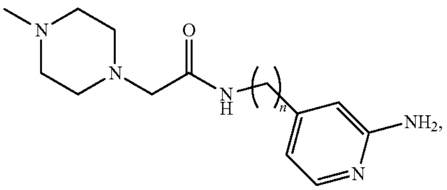

wherein n is between 0 and 10.

In an embodiment, the mass tag has a structure of

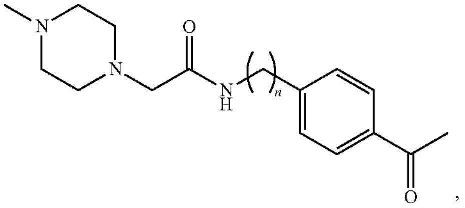

wherein n is between 0 and 10.

In an embodiment, the mass tag has a structure of

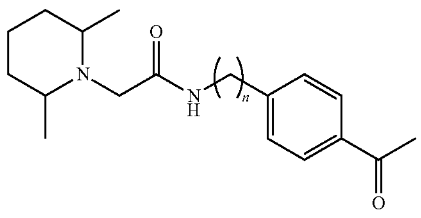

, wherein n is between 0 and 10.

In an embodiment, the mass tag has a structure of

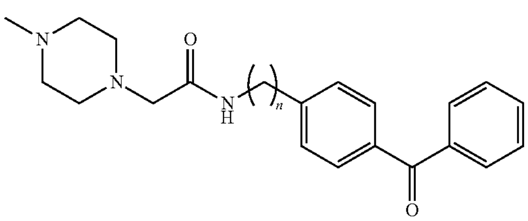

, wherein n is between 0 and 10.

In an embodiment, the mass tag has a structure of

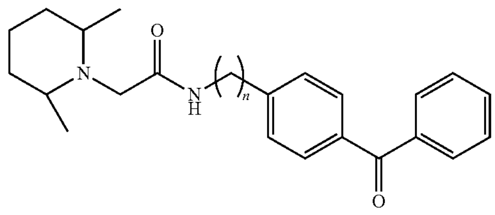

, wherein n is between 0 and 10.

In an embodiment, the mass tag has a structure of

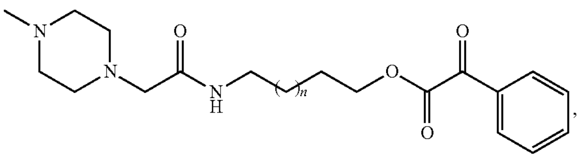

, wherein n is between 0 and 10.

In an embodiment, the mass tag has a structure of

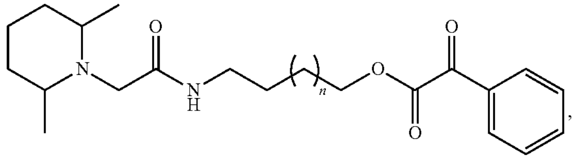

, wherein n is between 0 and 10.

In an embodiment, the mass tag has a structure of

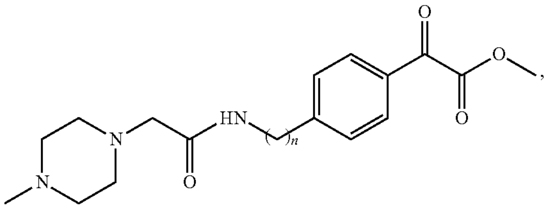

, wherein n is between 0 and 10.

In an embodiment, the mass tag has a structure of

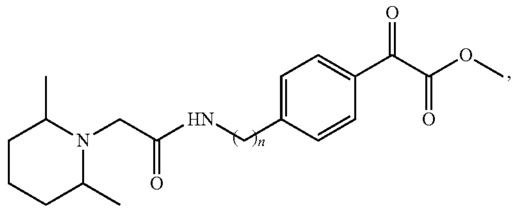

, wherein n is between 0 and 10.

In any of the embodiments of mass tag structures, "n" can be between 0 and 10 and any number therebetween. In an embodiment, n is between 0 and 9. In an embodiment, n is between 0 and 8. In an embodiment, n is between 0 and 7. In an embodiment, n is between 0 and 6. In an embodiment, n is between 0 and 5. In an embodiment, n is between 0 and 4. In an embodiment, n is between 0 and 3. In an embodiment, n is 10. In an embodiment, n is 9. In an embodiment, n is 8. In an embodiment, n is 7. In an embodiment, n is 6. In an embodiment, n is 5. In an embodiment, n is 4. In an embodiment, n is 3. In an embodiment, n is 2. In an embodiment, n is 1. In an embodiment, n is 0.

In an illustrative aspect, a method of quantifying one or more individual lipids from a composition of lipids is provided. The method comprises the steps of: combining the composition of lipids with one or more mass tags to form a tagged lipid composition, performing mass spectrometry on the tagged lipid composition to identify the one or more individual lipids, and quantifying the one or more individual lipids.

Any of the mass tags described above can be utilized with the method of quantifying one or more individual lipids from a composition of lipids. Furthermore, mass tags known and available and available for purchase are also known to the skilled artisan and can be alternatively utilized with the method of quantifying one or more individual lipids from a composition of lipids.

In an embodiment, the individual lipid is a lipid isomer. In an embodiment, the individual lipid is a neutral lipid. In an embodiment, the individual lipid is a polar lipid. In an embodiment, the individual lipid is a non-polar lipid. In an embodiment, the individual lipid comprises a low ionization capability.

In an embodiment, the composition of lipids comprises one or more unsaturated lipids. In an embodiment, the composition of lipids is blood. In an embodiment, the composition of lipids is plasma.

In an embodiment, the method does not require a lipid internal standard. In an embodiment, the lipid internal standard comprises stable isotope-labeled lipids. In an embodiment, the lipid internal standard comprises synthetic lipids.

In an embodiment, the mass spectrometry comprises tandem mass spectrometry. In an embodiment, the mass spectrometry is combined with high-performance liquid chromatography (HPLC).

In an embodiment, the method further comprises the step of identifying a double bond position of the one or more individual lipids. For instance, in this embodiment, the described method is capable of quantifying one or more individual lipids from a composition of lipids and also identifying a double bond position of the one or more individual lipids. In some aspects, the described method is capable of simultaneously quantifying and identifying. In an embodiment, the double bond position is a carbon-carbon double bond position.

In an illustrative aspect, a method of identifying a double bond position of an individual lipid is provided. The method comprises the steps of: combining a composition of lipids with one or more mass tags to form a tagged lipid composition, performing mass spectrometry on the tagged lipid composition to identify an individual lipid, and identifying the double bond position of the individual lipid.

Any of the mass tags described above can be utilized with the method of identifying a double bond position of an individual lipid. Furthermore, mass tags known and available and available for purchase are also known to the skilled artisan and can be alternatively utilized with the method of identifying a double bond position of an individual lipid.

In an embodiment, the double bond position is a carbon-carbon double bond position.

In an embodiment, the individual lipid is a lipid isomer. In an embodiment, the individual lipid is a neutral lipid. In an embodiment, the individual lipid is a polar lipid. In an embodiment, the individual lipid is a non-polar lipid. In an embodiment, the individual lipid comprises a low ionization capability.

In an embodiment, the composition of lipids comprises one or more unsaturated lipids. In an embodiment, the composition of lipids is blood. In an embodiment, the composition of lipids is plasma.

In an embodiment, the method does not require a lipid internal standard. In an embodiment, the lipid internal standard comprises stable isotope-labeled lipids. In an embodiment, the lipid internal standard comprises synthetic lipids.

In an embodiment, the mass spectrometry comprises tandem mass spectrometry. In an embodiment, the mass spectrometry is combined with high-performance liquid chromatography (HPLC).

In an embodiment, the method further comprises the step of quantifying one or more individual lipids from a composition of lipids. For instance, in this embodiment, the described method is capable of quantifying one or more individual lipids from a composition of lipids and also identifying a double bond position of the one or more individual lipids. In some aspects, the described method is capable of simultaneously quantifying and identifying.

In an illustrative aspect, a method of identifying a biological correlation of an individual lipid is provided. The method comprises the steps of: combining a composition of lipids with one or more mass tags to form a tagged lipid composition, performing mass spectrometry on the tagged lipid composition to identify the individual lipid, and identifying the double bond position of the individual lipid, quantifying the individual lipid, or a combination of both. The previously described embodiments of the method of quantifying one or more individual lipids from a composition of lipids and the method of identifying a double bond position of an individual lipid are applicable to the method of identifying a biological correlation of an individual lipid described herein.

Any of the mass tags described above can be utilized with the method of identifying a double bond position of an individual lipid. Furthermore, mass tags known and available and available for purchase are also known to the skilled artisan and can be alternatively utilized with the method of identifying a double bond position of an individual lipid.

For the method of identifying a biological correlation of an individual lipid, the biological correlation can be one or multiple correlations that are identifiable from a given sample. In an embodiment, the biological correlation is a disease biomarker. In an embodiment, the biological correlation is a disease prediction. In an embodiment, the biological correlation is a disease symptom prediction. In an embodiment, the biological correlation is a disease severity prediction. In an embodiment, the disease is cancer. In an embodiment, the disease is a cardiovascular disease. In an embodiment, the disease is an aging disease.

In an embodiment, the identified biological correlation of the individual lipid is compared to a composition comprising a control individual lipid. In an embodiment, the control individual lipid corresponds to a healthy patient or a healthy patient population. For instance, an individual lipid can be processed from a diseased patient or from a patient being evaluated for a disease and then compared to a healthy sample or a known standard previously obtained. In this manner, the method of identifying a biological correlation can be utilized as a predictive mechanism for human or animal health.

In an embodiment, the individual lipid is a lipid isomer. In an embodiment, the individual lipid is a neutral lipid. In an embodiment, the individual lipid is a polar lipid. In an embodiment, the individual lipid is a non-polar lipid. In an embodiment, the individual lipid comprises a low ionization capability.

In an embodiment, the composition of lipids comprises one or more unsaturated lipids. In an embodiment, the composition of lipids is blood. In an embodiment, the composition of lipids is plasma.

In an embodiment, the method does not require a lipid internal standard. In an embodiment, the lipid internal standard comprises stable isotope-labeled lipids. In an embodiment, the lipid internal standard comprises synthetic lipids.

In an embodiment, the mass spectrometry comprises tandem mass spectrometry. In an embodiment, the mass spectrometry is combined with high-performance liquid chromatography (HPLC).

In an illustrative aspect, a method of preparing a lipid derivative is provided. This method comprises the steps of: performing an aziridination reaction on an unsaturated lipid to form an aziridinated lipid, and applying a mass tag to the aziridinated lipid to form the lipid derivative. In an illustrative aspect, a second method of preparing a lipid derivative is provided. This method comprises the step of performing an aziridination reaction and applying a mass tag to an unsaturated lipid to form the lipid derivative. The previously described embodiments of the mass tags and the methods are applicable to the methods of preparing a lipid derivative described herein.

In an embodiment, mass spectrometry is performed on the lipid derivative. In an embodiment, the mass spectrometry comprises tandem mass spectrometry. In an embodiment, the mass spectrometry is combined with high-performance liquid chromatography (HPLC).
The following numbered embodiments are contemplated and are non-limiting:
1. A composition comprising a mass tag, wherein the mass tag has a structure selected from the group consisting of:
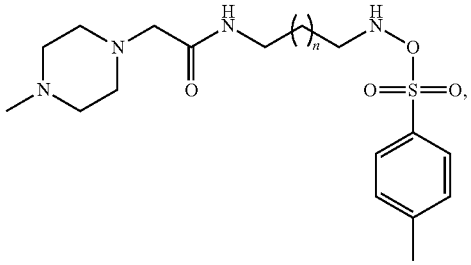
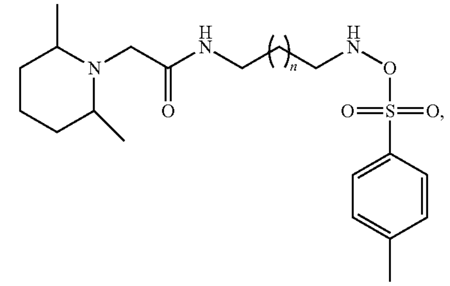
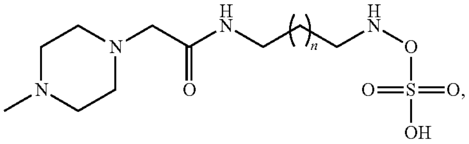
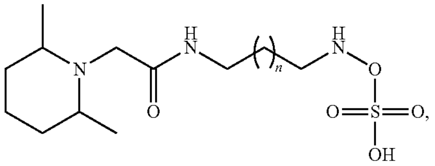
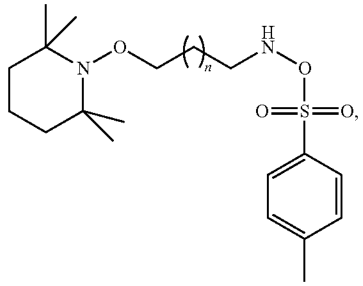
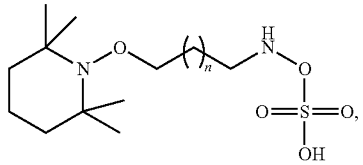
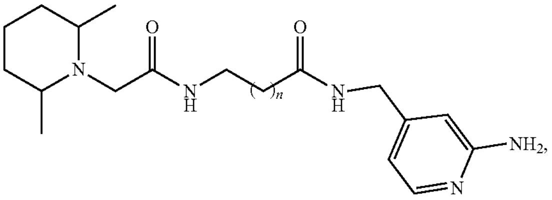
-continued
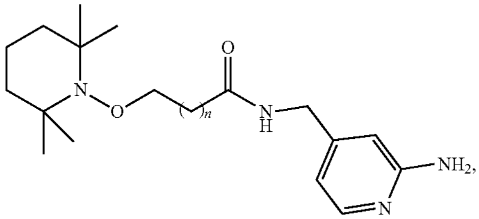
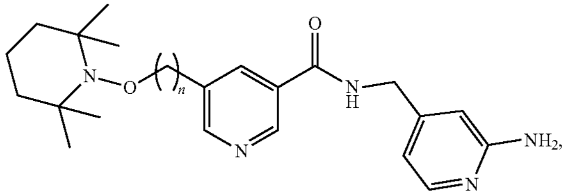
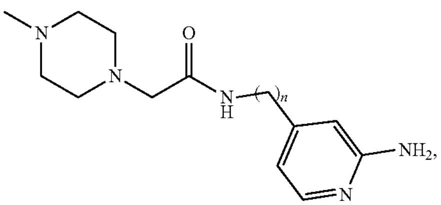
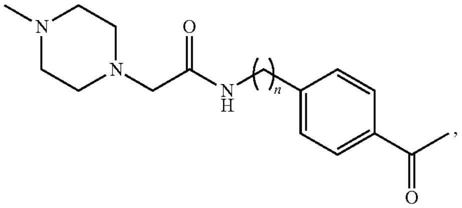
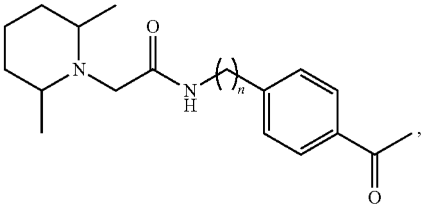
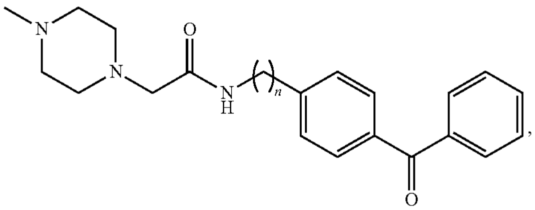
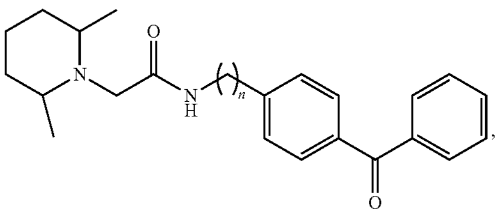
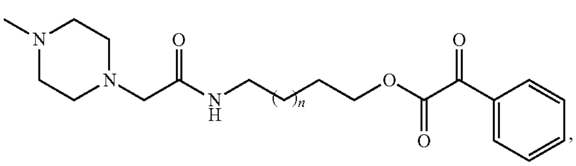

-continued

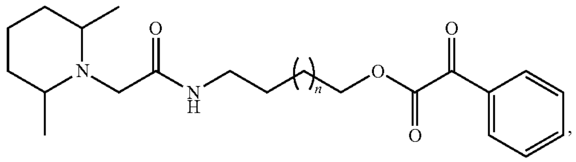

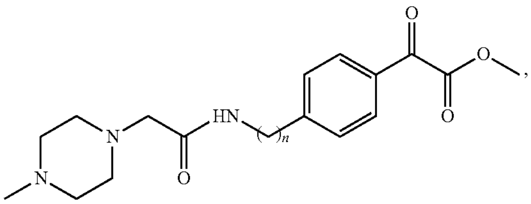

, and

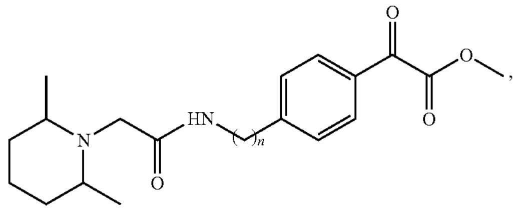

wherein n is between 0 and 10.

2. The composition of clause 1, any other suitable clause, or any combination of suitable clauses, wherein the mass tag has a structure selected from the group consisting of:

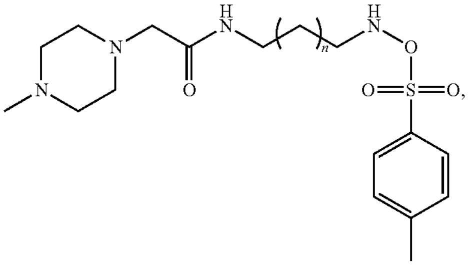

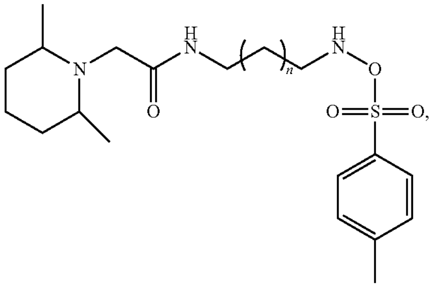

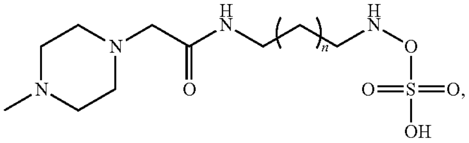

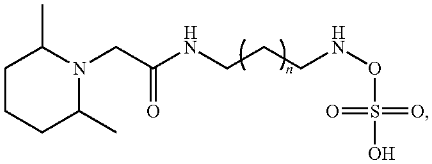

-continued

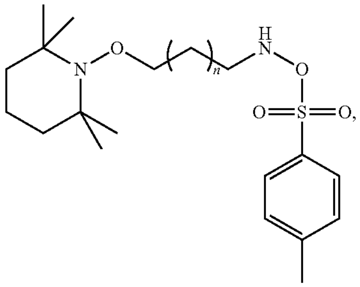

and

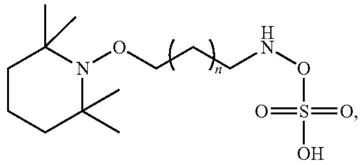

wherein n is between 0 and 10.

3. The composition of clause 1, any other suitable clause, or any combination of suitable clauses, the mass tag has a structure selected from the group consisting of:

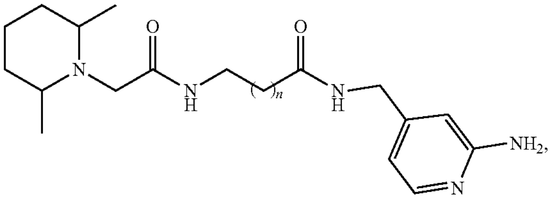

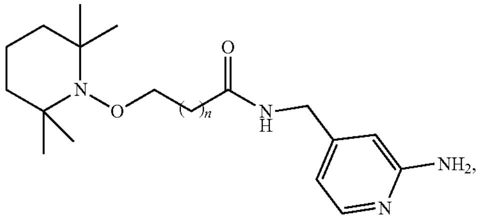

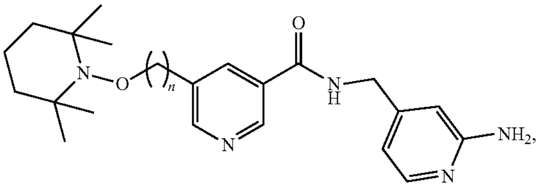

and

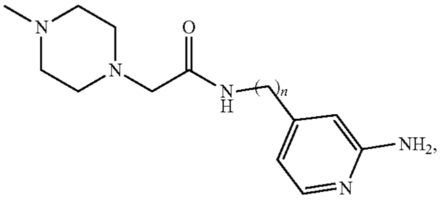

wherein n is between 0 and 10.

4. The composition of clause 1, any other suitable clause, or any combination of suitable clauses, the mass tag has a structure selected from the group consisting of:

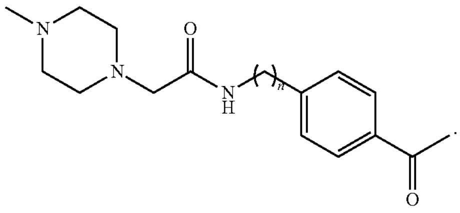

.

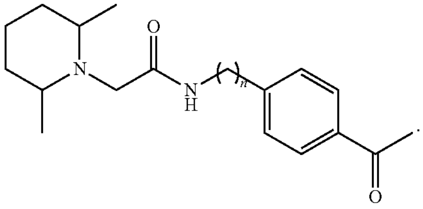

.

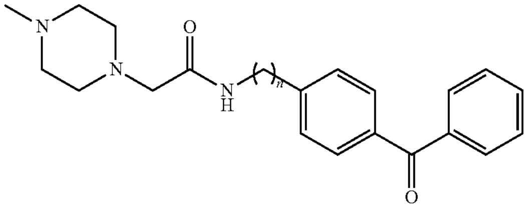

.

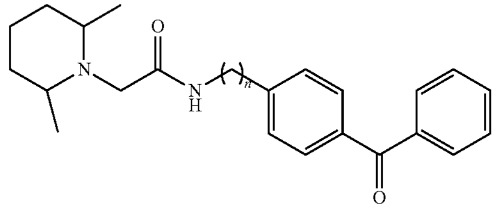

.

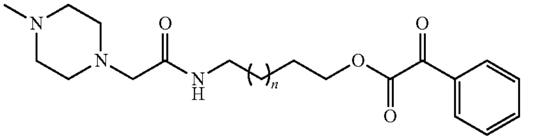

,

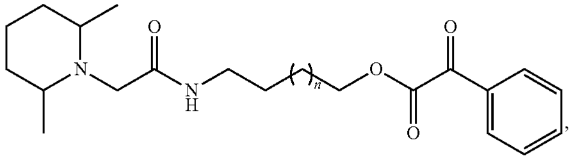

,

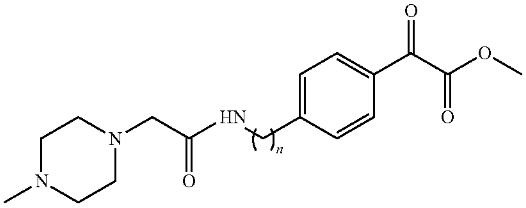

, and

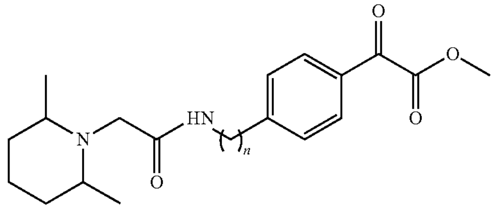

.

wherein n is between 0 and 10.

5. The composition of clause 1, any other suitable clause, or any combination of suitable clauses, the mass tag has a structure of

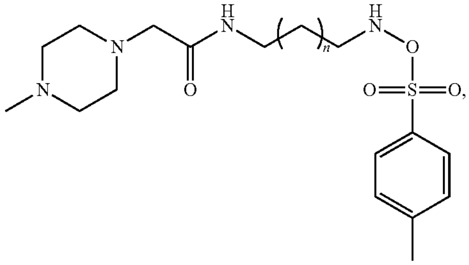

wherein n is between 0 and 10.

6. The composition of clause 1, any other suitable clause, or any combination of suitable clauses, the mass tag has a structure of

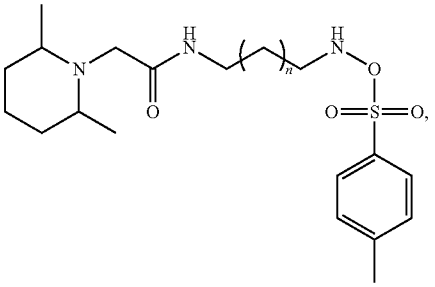

wherein n is between 0 and 10.

7. The composition of clause 1, any other suitable clause, or any combination of suitable clauses, the mass tag has a structure of

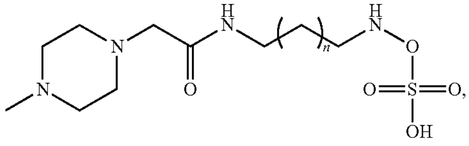

wherein n is between 0 and 10.

8. The composition of clause 1, any other suitable clause, or any combination of suitable clauses, the mass tag has a structure of

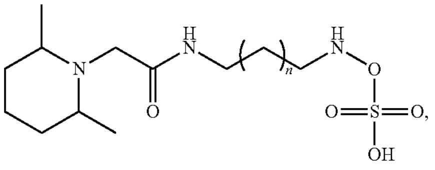

wherein n is between 0 and 10.

9. The composition of clause 1, any other suitable clause, or any combination of suitable clauses, the mass tag has a structure of

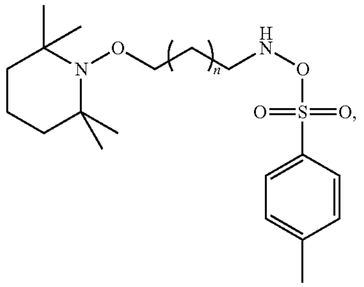

wherein n is between 0 and 10.

10. The composition of clause 1, any other suitable clause, or any combination of suitable clauses, the mass tag has a structure of

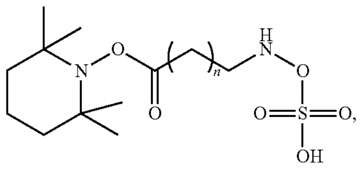

wherein n is between 0 and 10.

11. The composition of clause 1, any other suitable clause, or any combination of suitable clauses, the mass tag has a structure of

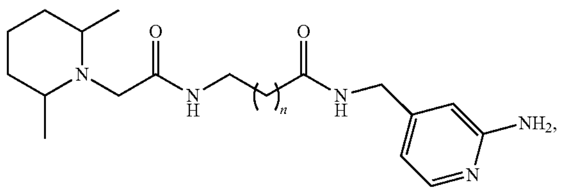

wherein n is between 0 and 10.

12. The composition of clause 1, any other suitable clause, or any combination of suitable clauses, the mass tag has a structure of

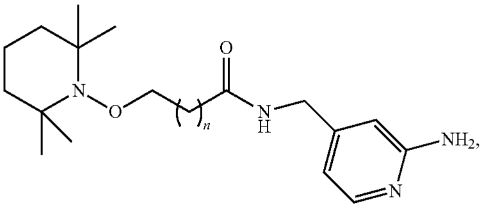

wherein n is between 0 and 10.

13. The composition of clause 1, any other suitable clause, or any combination of suitable clauses, the mass tag has a structure of

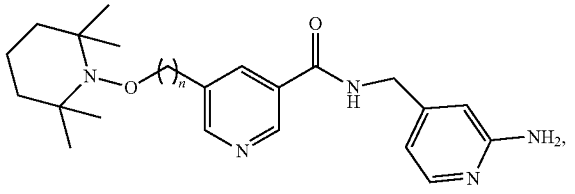

wherein n is between 0 and 10.

14. The composition of clause 1, any other suitable clause, or any combination of suitable clauses, the mass tag has a structure of

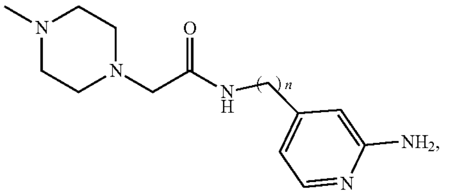

wherein n is between 0 and 10.

15. The composition of clause 1, any other suitable clause, or any combination of suitable clauses, the mass tag has a structure of

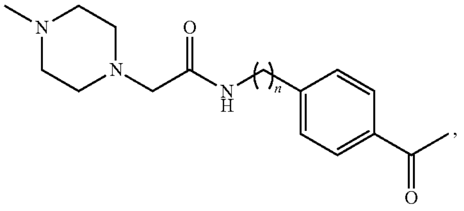

wherein n is between 0 and 10.

16. The composition of clause 1, any other suitable clause, or any combination of suitable clauses, the mass tag has a structure of

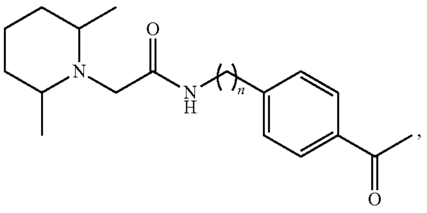

wherein n is between 0 and 10.

17. The composition of clause 1, any other suitable clause, or any combination of suitable clauses, the mass tag has a structure of

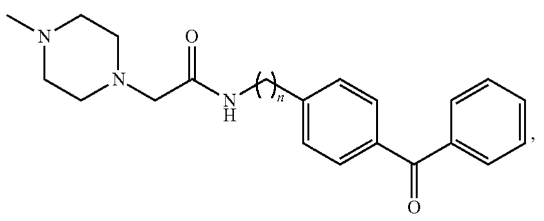

wherein n is between 0 and 10.

18. The composition of clause 1, any other suitable clause, or any combination of suitable clauses, the mass tag has a structure of

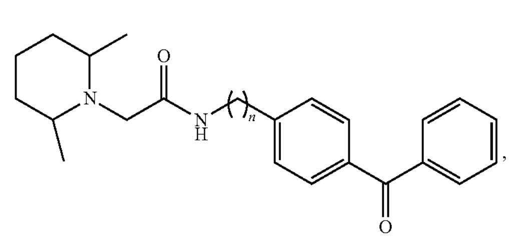

wherein n is between 0 and 10.

19. The composition of clause 1, any other suitable clause, or any combination of suitable clauses, the mass tag has a structure of

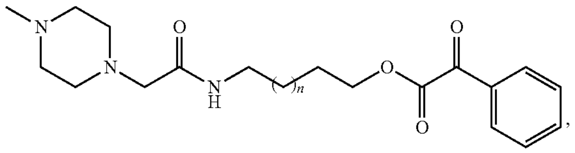

wherein n is between 0 and 10.

20. The composition of clause 1, any other suitable clause, or any combination of suitable clauses, the mass tag has a structure of

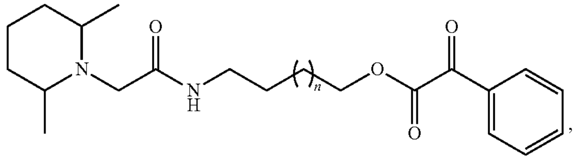

wherein n is between 0 and 10.

21. The composition of clause 1, any other suitable clause, or any combination of suitable clauses, the mass tag has a structure of

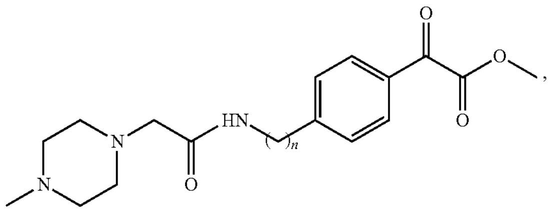

wherein n is between 0 and 10.

22. The composition of clause 1, any other suitable clause, or any combination of suitable clauses, the mass tag has a structure of

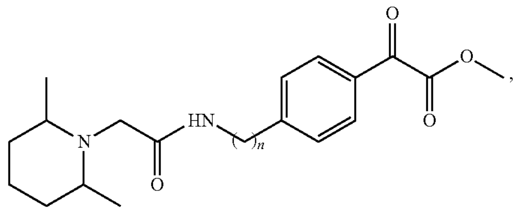

wherein n is between 0 and 10.

23. The composition of any one of clauses 1 to 22, any other suitable clause, or any combination of suitable clauses, wherein n is between 0 and 9.

24. The composition of any one of clauses 1 to 22, any other suitable clause, or any combination of suitable clauses, wherein n is between 0 and 8.

25. The composition of any one of clauses 1 to 22, any other suitable clause, or any combination of suitable clauses, wherein n is between 0 and 7.

26. The composition of any one of clauses 1 to 22, any other suitable clause, or any combination of suitable clauses, wherein n is between 0 and 6.

27. The composition of any one of clauses 1 to 22, any other suitable clause, or any combination of suitable clauses, wherein n is between 0 and 5.

28. The composition of any one of clauses 1 to 22, any other suitable clause, or any combination of suitable clauses, wherein n is between 0 and 4.

29. The composition of any one of clauses 1 to 22, any other suitable clause, or any combination of suitable clauses, wherein n is between 0 and 3.

30. The composition of any one of clauses 1 to 22, any other suitable clause, or any combination of suitable clauses, wherein n is 10.

31. The composition of any one of clauses 1 to 22, any other suitable clause, or any combination of suitable clauses, wherein n is 9.

32. The composition of any one of clauses 1 to 22, any other suitable clause, or any combination of suitable clauses, wherein n is 8.

33. The composition of any one of clauses 1 to 22, any other suitable clause, or any combination of suitable clauses, wherein n is 7.

34. The composition of any one of clauses 1 to 22, any other suitable clause, or any combination of suitable clauses, wherein n is 6.

35. The composition of any one of clauses 1 to 22, any other suitable clause, or any combination of suitable clauses, wherein n is 5.
36. The composition of any one of clauses 1 to 22, any other suitable clause, or any combination of suitable clauses, wherein n is 4.
37. The composition of any one of clauses 1 to 22, any other suitable clause, or any combination of suitable clauses, wherein n is 3.
38. The composition of any one of clauses 1 to 22, any other suitable clause, or any combination of suitable clauses, wherein n is 2.
39. The composition of any one of clauses 1 to 22, any other suitable clause, or any combination of suitable clauses, wherein n is 1.
40. The composition of any one of clauses 1 to 22, any other suitable clause, or any combination of suitable clauses, wherein n is 0.
41. A method of quantifying one or more individual lipids from a composition of lipids, said method comprising the steps of:
combining the composition of lipids with one or more mass tags to form a tagged lipid composition,
performing mass spectrometry on the tagged lipid composition to identify the one or more individual lipids, and
quantifying the one or more individual lipids.
42. The method of clause 41, any other suitable clause, or any combination of suitable clauses, wherein the individual lipid is a lipid isomer.
43. The method of clause 41, any other suitable clause, or any combination of suitable clauses, wherein the individual lipid is a neutral lipid.
44. The method of clause 41, any other suitable clause, or any combination of suitable clauses, wherein the individual lipid is a polar lipid.
45. The method of clause 41, any other suitable clause, or any combination of suitable clauses, wherein the individual lipid is a non-polar lipid.
46. The method of clause 41, any other suitable clause, or any combination of suitable clauses, wherein the individual lipid comprises a low ionization capability.
47. The method of clause 41, any other suitable clause, or any combination of suitable clauses, wherein the composition of lipids comprises one or more unsaturated lipids.
48. The method of clause 41, any other suitable clause, or any combination of suitable clauses, wherein the composition of lipids is blood.
49. The method of clause 41, any other suitable clause, or any combination of suitable clauses, wherein the composition of lipids is plasma.
50. The method of clause 41, any other suitable clause, or any combination of suitable clauses, wherein the method does not require a lipid internal standard.
51. The method of clause 50, any other suitable clause, or any combination of suitable clauses, wherein the lipid internal standard comprises stable isotope-labeled lipids.
52. The method of clause 50, any other suitable clause, or any combination of suitable clauses, wherein the lipid internal standard comprises synthetic lipids.
53. The method of clause 41, any other suitable clause, or any combination of suitable clauses, wherein the mass spectrometry comprises tandem mass spectrometry.
54. The method of clause 41, any other suitable clause, or any combination of suitable clauses, wherein the mass spectrometry is combined with high-performance liquid chromatography (HPLC).
55. The method of clause 41, any other suitable clause, or any combination of suitable clauses, wherein the method further comprises the step of identifying a double bond position of the one or more individual lipids.
56. The method of clause 55, any other suitable clause, or any combination of suitable clauses, wherein the double bond position is a carbon-carbon double bond position.
157. A method of identifying a double bond position of an individual lipid, said method comprising the steps of:
combining a composition of lipids with one or more mass tags to form a tagged lipid composition,
performing mass spectrometry on the tagged lipid composition to identify an individual lipid, and
identifying the double bond position of the individual lipid.
58. The method of clause 57, any other suitable clause, or any combination of suitable clauses, wherein the double bond position is a carbon-carbon double bond position.
59. The method of clause 57, any other suitable clause, or any combination of suitable clauses, wherein the individual lipid is a lipid isomer.
60. The method of clause 57, any other suitable clause, or any combination of suitable clauses, wherein the individual lipid is a neutral lipid.
61. The method of clause 57, any other suitable clause, or any combination of suitable clauses, wherein the individual lipid is a polar lipid.
62. The method of clause 57, any other suitable clause, or any combination of suitable clauses, wherein the individual lipid is a non-polar lipid.
63. The method of clause 57, any other suitable clause, or any combination of suitable clauses, wherein the individual lipid comprises a low ionization capability.
64. The method of clause 57, any other suitable clause, or any combination of suitable clauses, wherein the composition of lipids comprises one or more unsaturated lipids.
65. The method of clause 57, any other suitable clause, or any combination of suitable clauses, wherein the composition of lipids is blood.
66. The method of clause 57, any other suitable clause, or any combination of suitable clauses, wherein the composition of lipids is plasma.
67. The method of clause 57, any other suitable clause, or any combination of suitable clauses, wherein the method does not require a lipid internal standard.
68. The method of clause 67, any other suitable clause, or any combination of suitable clauses, wherein the lipid internal standard comprises stable isotope-labeled lipids.
69. The method of clause 67, any other suitable clause, or any combination of suitable clauses, wherein the lipid internal standard comprises synthetic lipids.
70. The method of clause 57, any other suitable clause, or any combination of suitable clauses, wherein the mass spectrometry comprises tandem mass spectrometry.
71. The method of clause 57, any other suitable clause, or any combination of suitable clauses, wherein the mass spectrometry is combined with high-performance liquid chromatography (HPLC).
72. The method of clause 57, any other suitable clause, or any combination of suitable clauses, wherein the method further comprises the step of quantifying the one or more individual lipids.

73. A method of identifying a biological correlation of an individual lipid, said method comprising the steps of:
combining a composition of lipids with one or more mass tags to form a tagged lipid composition,
performing mass spectrometry on the tagged lipid composition to identify the individual lipid, and
identifying the double bond position of the individual lipid, quantifying the individual lipid, or a combination of both.

74. The method of clause 73, any other suitable clause, or any combination of suitable clauses, wherein the identified biological correlation of the individual lipid is compared to a composition comprising a control individual lipid.

75. The method of clause 74, any other suitable clause, or any combination of suitable clauses, wherein the control individual lipid corresponds to a healthy patient or a healthy patient population.

76. The method of clause 73, any other suitable clause, or any combination of suitable clauses, wherein the biological correlation is a disease biomarker.

77. The method of clause 73, any other suitable clause, or any combination of suitable clauses, wherein the biological correlation is a disease prediction.

78. The method of clause 73, any other suitable clause, or any combination of suitable clauses, wherein the biological correlation is a disease symptom prediction.

79. The method of clause 73, any other suitable clause, or any combination of suitable clauses, wherein the biological correlation is a disease severity prediction.

80. The method of clause 73, any other suitable clause, or any combination of suitable clauses, wherein the disease is cancer.

81. The method of clause 73, any other suitable clause, or any combination of suitable clauses, wherein the disease is a cardiovascular disease.

82. The method of clause 73, any other suitable clause, or any combination of suitable clauses, wherein the disease is an aging disease.

83. The method of clause 73, any other suitable clause, or any combination of suitable clauses, wherein the individual lipid is a lipid isomer.

84. The method of clause 73, any other suitable clause, or any combination of suitable clauses, wherein the individual lipid is a neutral lipid.

85. The method of clause 73, any other suitable clause, or any combination of suitable clauses, wherein the individual lipid is a polar lipid.

86. The method of clause 73, any other suitable clause, or any combination of suitable clauses, wherein the individual lipid is a non-polar lipid.

87. The method of clause 73, any other suitable clause, or any combination of suitable clauses, wherein the individual lipid comprises a low ionization capability.

88. The method of clause 73, any other suitable clause, or any combination of suitable clauses, wherein the composition of lipids comprises one or more unsaturated lipids.

89. The method of clause 73, any other suitable clause, or any combination of suitable clauses, wherein the composition of lipids is blood.

90. The method of clause 73, any other suitable clause, or any combination of suitable clauses, wherein the composition of lipids is plasma.

91. The method of clause 73, any other suitable clause, or any combination of suitable clauses, wherein the method does not require a lipid internal standard.

92. The method of clause 91, any other suitable clause, or any combination of suitable clauses, wherein the lipid internal standard comprises stable isotope-labeled lipids.

93. The method of clause 91, any other suitable clause, or any combination of suitable clauses, wherein the lipid internal standard comprises synthetic lipids.

94. The method of clause 73, any other suitable clause, or any combination of suitable clauses, wherein the mass spectrometry comprises tandem mass spectrometry.

95. The method of clause 73, any other suitable clause, or any combination of suitable clauses, wherein the mass spectrometry is combined with high-performance liquid chromatography (HPLC).

96. A method of preparing a lipid derivative, said method comprising the steps of:
performing an aziridination reaction on an unsaturated lipid to form an aziridinated lipid,
applying a mass tag to the aziridinated lipid to form the lipid derivative.

97. The method of clause 96, any other suitable clause, or any combination of suitable clauses, wherein mass spectrometry is performed on the lipid derivative.

98. The method of clause 97, any other suitable clause, or any combination of suitable clauses, wherein the mass spectrometry comprises tandem mass spectrometry.

99. The method of clause 97, any other suitable clause, or any combination of suitable clauses, wherein the mass spectrometry is combined with high-performance liquid chromatography (HPLC).

100. A method of preparing a lipid derivative, said method comprising the step of performing an aziridination reaction and applying a mass tag to an unsaturated lipid to form the lipid derivative.

101. The method of clause 100, any other suitable clause, or any combination of suitable clauses, wherein mass spectrometry is performed on the lipid derivative.

102. The method of clause 101, any other suitable clause, or any combination of suitable clauses, wherein the mass spectrometry comprises tandem mass spectrometry.

103. The method of clause 101, any other suitable clause, or any combination of suitable clauses, wherein the mass spectrometry is combined with high-performance liquid chromatography (HPLC).

Example 1

Materials and Methods for Aziridination and Mass Tagging of Lipids and Associated Analyses The instant example provides exemplary materials and methods for performing an aziridination reaction and applying a mass tag to form lipid derivatives. Exemplary processes for quantification and identification are also provided.

Exemplary Process for the Synthesis of Lipid Aziridines

Lipid standard with leq C=C bonds was dissolved with HFIP. HOSA (1.5 eq), pyridine (3 eq) and ethyl trifluoro pyruvate (20% eq). The reaction mixture was stirred under 50 degrees Celsius overnight. When Rh2esp2 (5%) was used as a catalyst, the reaction mixture was stirred at room temperature overnight. Ethyl oleate aziridine was purified by column chromatography. The elution solvent used was ethyl acetate/hexane (v/v=1/4).

Exemplary Process of Generating TMT-Labeled Lipids for Relative Quantification

Aziridination reaction mixture with lipid concentrations of 5 mM and 10 mM from two vials (with catalyst ethyl trifluoro pyruvate) was diluted with acetonitrile by 200 times. Then 100 μL of diluted solution was transferred to vials, respectively. A rotary evaporator was used to remove solvent. Noted that HFIP can react with tandem mass tag, vacuum was applied to remove HFIP. 495 μL acetonitrile was added to vials, acquiring lipid aziridine concentration of 5 μM and 10 μM, followed with 4.35 μL 57.2 mM tags (50 equivalence), 126-tag added to one vial while the other vial was added with 127-tag (126 and 127 indicate the mass of mass reporters). The reaction mixture was stirred at 50 degrees Celsius for two hours. The same amount of volume of reaction mixture were mixed for MS and MS/MS analysis.

Exemplary Lipid Extraction from Human Plasma

Cholesterol ester (CE) lipid extraction method from human plasma used an ethyl acetate/isooctane (1/3, v/v) solvent system. Briefly, 2 mL water was added to 50 μL human plasma, followed with the addition of 2 mL ethyl acetate/isooctane (1/3, v/v). The mixture was vortex-mixed for 2 minutes and then was centrifuged at 3000 rpm for 10 minutes. The upper layer was collected. The aqueous layer was extracted with 2 mL ethyl acetate/isooctane (1/3, v/v) and collected as an organic layer. The aqueous phase extraction step was repeated. The organic layer was dried under a nitrogen stream. The lipid extracts were redissolved in 2 mL chloroform/methanol (2/1), followed by 20 times dilution for LC-MS analysis.

HPLC-MS Conditions

Mass spectrometry analysis was performed on Orbitrap Velos Pro (Thermo Fisher Scientific). For lipid standards, samples were ionized using a home-built nano electrospray ionization source (nanoESI) and spray voltage of nanoESI was around 1.5 kV. The following MS parameters were used for data acquisitions: S-lens RF level was set to be 67.9%, and capillary temperature was set at 200° C. Full MS scans were acquired at m/z 100-2000 with resolving power of 60000. Maximum injection time of 500 ms and 1 micro-scan were used for full MS scans. For lipid identification, MS/MS and MS/MS/MS acquisitions were performed upon CID. For lipid quantification, MS/MS acquisitions were performed upon HCD. The HCD energy used for fragmentation was 60 manufactural units.

A vanquish UHPLC system (Thermo Fisher Scientific) combined with a Orbitrap Velos Pro mass spectrometer (Thermo Fisher Scientific) was applied for LC-MS analysis of human plasma biological samples. An aliquot of 5 μL of sample was injected into the Accucore C30 column (Thermo Fisher Scientific, C30, 2.1 mm×150 mm, 2.6 μm). The mobile phase used was acetonitrile/water (60/40, v/v) (solvent A) and isopropanol/acetonitrile (90/10, v/v) (solvent B), both contain 10 mM ammonium formate and 0.1% formic acid. The column separation was carried out at 40° C. with a flow rate of 0.2 m/min. The elute gradient was as follows: 30-50% B at 0-3 min (to waste), 50-70% B at 3-7 min, 70-99% B at 7-12 min, 99% B at 12-20 min, 99-70% B at 20-25 min, 70-30% B at 25-28 min and 30% B at 28-30 min. Sheath gas, auxiliary gas and sweep gas flow rate were set as 35, 10 and 1 arb respectively. The applied voltage is 3 kV and capillary temperature is 275 degrees Celsius, while S-lens RF Level is 60%. Data dependent acquisition (DDA) was performed for lipid extracts before reaction. A cycle combines one full MS scan and three MS/MS scans. Full MS scans were acquired at m/z 100-2000 with resolving power of 30000. HCD MS/MS scans were applied with 15000 resolving power and 35 normalized collision energy. For lipid aziridine sample analysis, the parent mass list was imported to data dependent setting so that CID tandem mass spectra of lipid aziridine (MS2) and lipid acyl chain (MS3) can be targeted. Normalized collision energy was set to 35-40 in MS/MS scans and 35 in MS/MS/MS scans. After TMT tagging, a mass list of products was imported to global non-data dependent setting. Once full spectrum is collected with resolving power 30000, HCD MS/MS scans with 60 normalized collision energy were followed for all the masses in the list with resolving power 15000 to detect mass reports.

Example 2

Identification of C═C Double Bond Positions of Lipids

Ethyl oleate is produced in the body after intake of ethanol. However, due to poor ionization efficiency, the lipid is typically not detectible via MS. For the instant example, identification of C═C double bond positions was evaluated using the described methods.

Figure 2A:
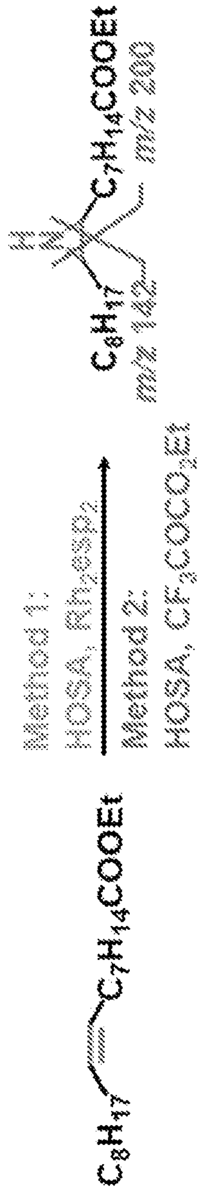

First, aziridination was used to activate C═C bonds. For the instant example, Rh2esp2 and organocatalyst ethyl trifluoro pyruvate were examined for catalyzing aziridination (see FIG. 2A).

Based on the full mass spectrum of the reaction mixture, ethyl oleate aziridine was formed with m/z 326 using either catalyst, and the product peak was identified as the base peak to demonstrate the improved ionization efficiency of lipid. (see FIG. 2B). To obtain the positional information of C═C bond, ethyl oleate aziridine was then isolated and fragmented via CID. The major fragment peak m/z 280 was generated due to the breakage of ester bond.

Figures 2B, 2C:
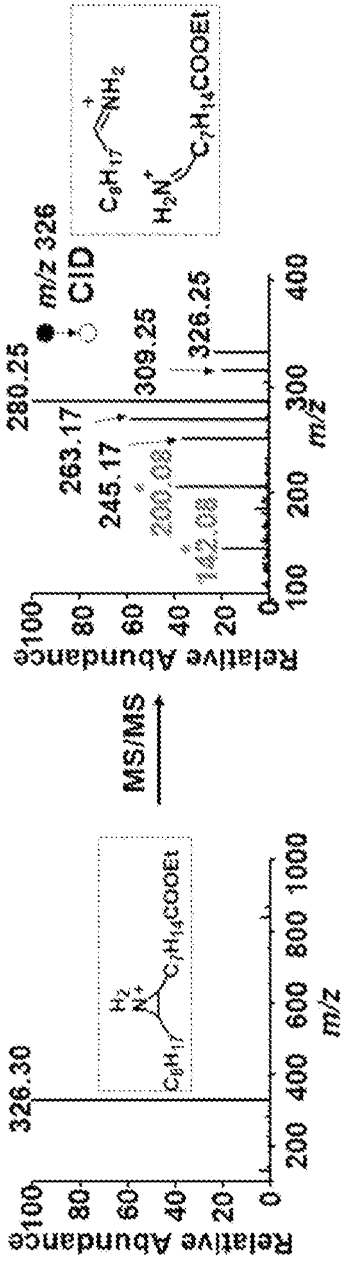
Figures 3A, 3B, 3C:
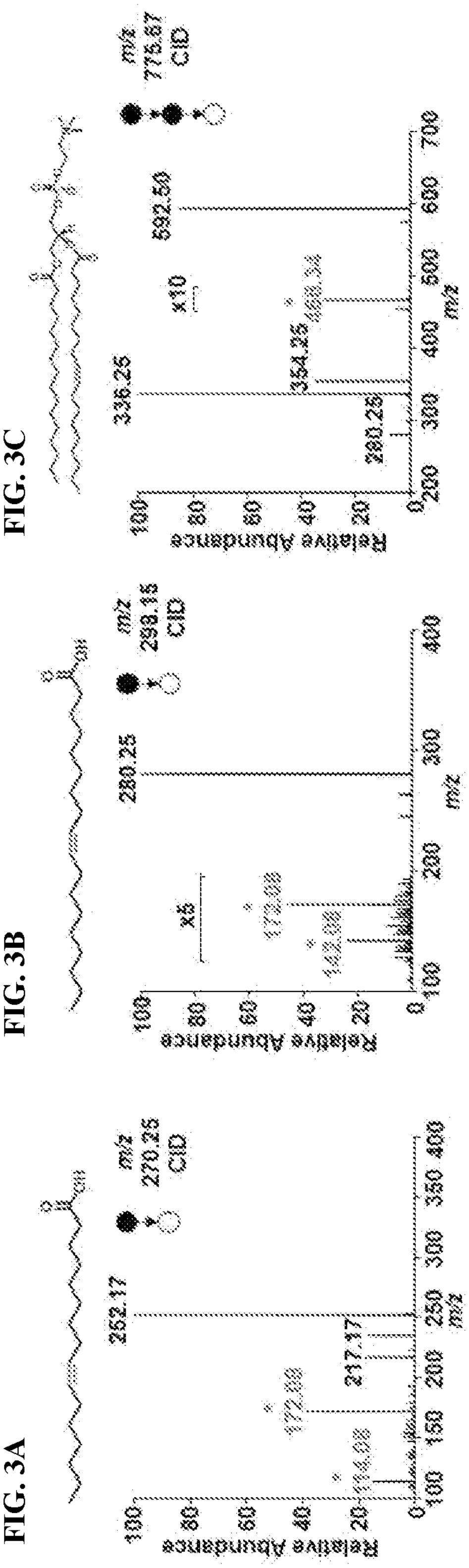
FIGS. 3A-3I show CID tandem mass spectra of different types of lipid aziridines
Figures 3D, 3E, 3F:
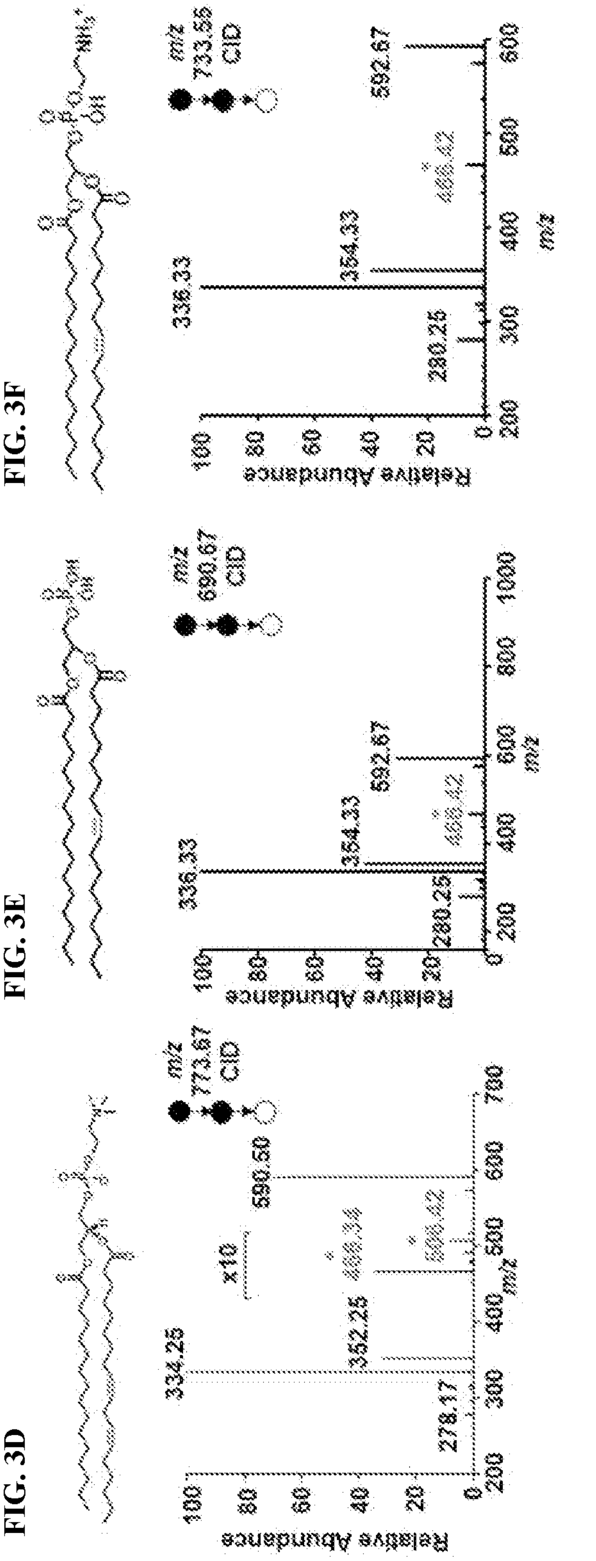
Figures 3G, 3H, 3I:
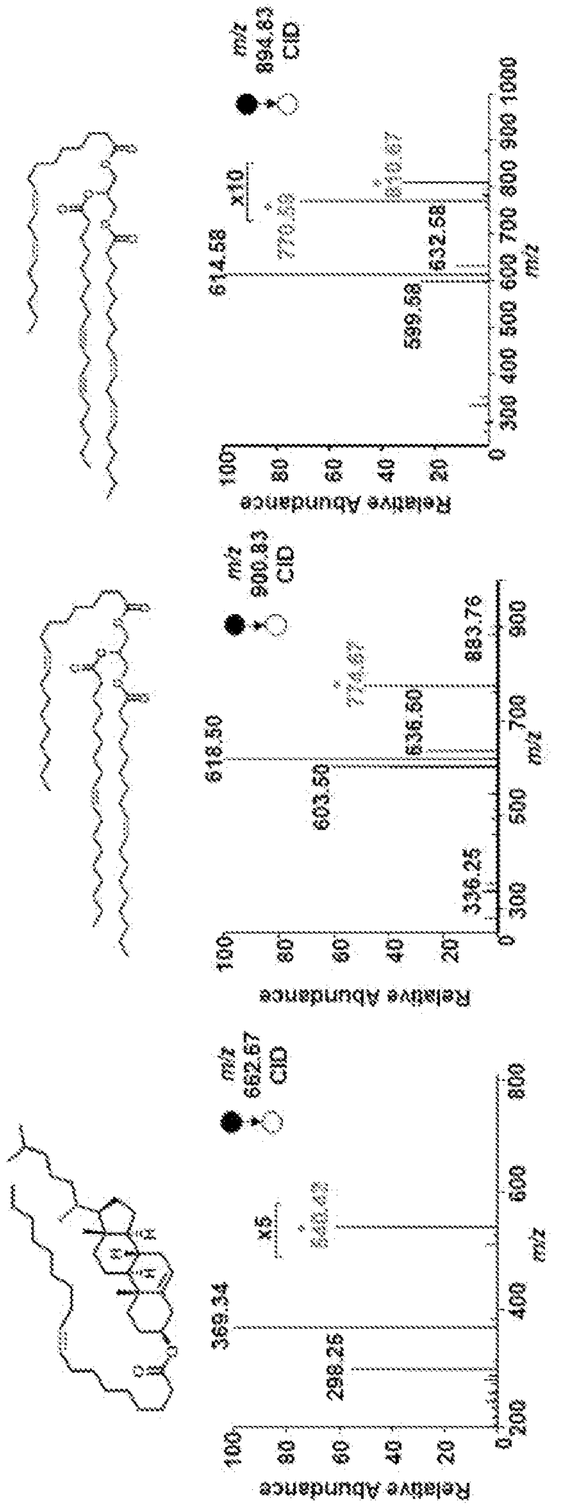

Followed with losing $NH_2$ in the aziridine ring on the basis of m/z 280 can give m/z 263; with further cleavage of the carbonyl group, peak m/z 245 can be detected. The peak m/z 309 is shown due to losing a $NH_2$ from aziridine. A pair of diagnostic ions with m/z 142 and 200 are also observed due to aziridine ring opening. The structures of diagnostic ions are shown in FIG. 2C. The result demonstrated that aziridination reaction is able to visualize lipids with poor ionization efficiency and, at the same time, identify C═C bond positional isomers in unsaturated lipids.

Ethyl oleate only contains one C═C bond, so there is only one possibility for the product, mono-aziridination product. However, if there are multiple C═C bonds present in one lipid, the product with different aziridination degrees may give different mass reporter ratios in HCD after labeling. In this case, the ideal situation is that only products with the same aziridination degree will be obtained.

Cholesterol ester (CE) 18:2 (9Z, 12Z) lipid has three C═C bonds in the lipid, so it was used as a representative for lipids with multiple C═C bonds. Two aziridination methods with different catalysts were applied to CE 18:2. From the spectra, peaks of m/z 664, 679, 694 can be seen with rhodium catalyst, which corresponds to mono-, di-, tri-aziridination products, respectively. Surprisingly, when an organocatalyst was applied, only a mono-aziridination product was observed.

Thereafter, it was evaluated whether aziridine functional groups have been introduced at each of the C═C bond position. In this regard, CID fragmentation of m/z 664 was performed. FIG. 2D shows that peak m/z 296 and m/z 369 are two of most abundant peaks, which are produced due to the cleavage of C═O while the aziridine is in the chain.

With ester bond breaking, m/z 278 is observed and at this situation the aziridine is also in the chain. The presence of m/z 384 is because of the C═O bond breaking while the aziridine is on a six-membered ring. (FIG. 2E). Peaks m/z 540 and 580 are observed with the aziridine ring opening. These two diagnostic ions tell the positions of C═C bonds. From the fragmentation results, aziridine can be formed on any C═C bond positions and diagnostic ions can be obtained. Notably, cholesterol ester lipid is a typical non-polar lipid which cannot be easily detected by MS. As a result, the described methods are capable of analyzing lipids with poor ionization efficiency.

To test the versatility of the described methods, different types of lipids were also selected for demonstration. (see FIGS. 3A-3I). Briefly, aziridination reactions were performed in the same conditions used for ethyl oleate and CE 18:2. After the reaction was completed, tandem mass spectra of different lipid aziridines were displayed and diagnostic ions for FA 16:1 (9Z), FA 18:1 (9Z), PC 16:0/18:1 (9Z), PC 16:0/18:2 (9Z,12Z), PA 16:0/18:1 (9Z), PE 16:0-18:1 (9Z), CE 18:1 (9Z), TG 18:1 (9Z)/18:1 (9Z)/18:1 (9Z), TG 18:2 (9Z, 12Z)/18:2 (9Z, 12Z)/18:2 (9Z, 12Z) were all observed and labeled (see stars in FIGS. 3A-3I). Accordingly, the described methods are capable of identifying C═C bond positions for different categories of lipids.

Example 3

Efficacy of Lipid Relative Quantification

To examine the feasibility of the described methods in relative quantification, ethyl oleate solutions with different concentrations were employed. Ethyl oleate was dissolved in the Hexafluoroisopropanol (HFIP), obtaining concentrations of 5 mM and 10 mM. Aziridination reactions using organocatalyst as catalyst were performed in each vial. Except for the different lipid substrate concentrations, all other experimental conditions were the same, including the amount of reagent added and the reaction conditions. Aziridination was reacted overnight, followed by tagging.

Figures 4A, 4B, 4C:
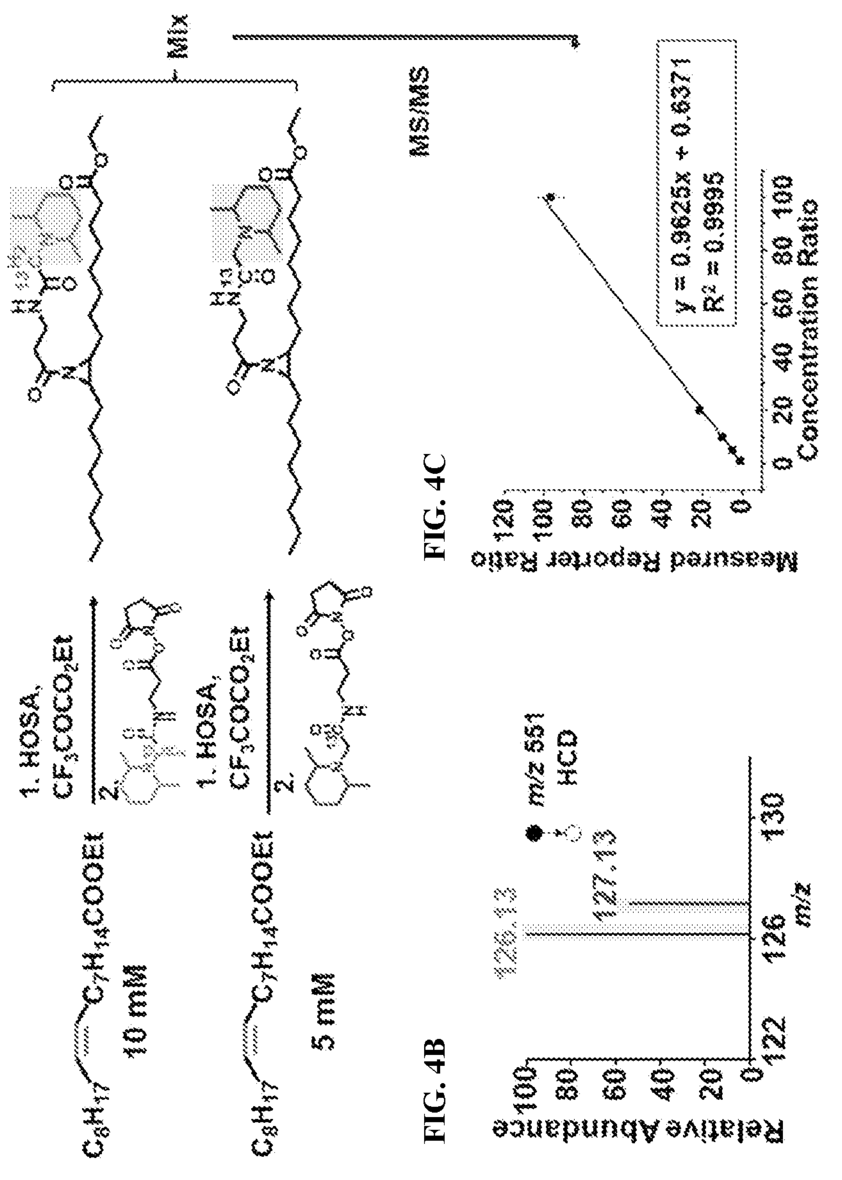
FIGS. 4A-4C show relative quantification of mass tagged ethyl oleate.

Various structures of mass tags are shown in FIG. 4A. Although two tags have the same chemical structure, they have different distributions of isobaric carbon: one tag has an isobaric carbon in the mass reporter region while the other has it in the mass balancer part. This ensures the tagged lipids from two vials shares same mass and m/z of mass reporters differ.

With two hours of labeling reaction, the same amount of reaction mixture from two vials was combined and detected with nano-electrospray ionization (nanoESI). Tagged lipid with m/z 551 was observed in the full mass spectrum. Because the masses of mass reporters are low, CID is not suitable due to its low mass cut-off phenomenon. Thus, HCD is applied to detect mass reporters. The collision energy of HCD is optimized at 60 V at which mass reporters are the main fragment from the tag which is indicative of the accuracy of quantification.

In tandem mass spectrum, mass reporter ions at m/z 126 and 127 are clearly observed (FIG. 4B). Three nanoESI detections were performed in parallel for the sample to reduce random error. The averaged ratio of mass reporter is 1.85 which gives relative error within 10% comparing with the original lipid ratio, 2. The quantification result showed that the quantity ratios of the lipids can be known by measuring mass reporter ratio.

To further validate the power of method in quantifying lipids with a broad range of concentrations, ethyl oleate aziridine was synthesized and purified. Different concentrations of aziridine solutions were prepared (0.1 μM, 0.5 μM, 1 μM, 2 μM, 10 μM) and the concentration ratios from 1:1 to 1:100 were obtained. Ratios at 1:1, 1:5, 1:10, 1:20, 1:100 were chosen for the instant example. The correlation between measured ratios of mass reporters and expected concentration ratios of lipid aziridine is shown in FIG. 4C. A linear relationship is presented with a R2 equals to 0.9995 and slope equals to 0.96, demonstrating it was capable of accurately obtaining relative quantification of lipids in two orders of magnitude dynamic range.

Furthermore, relative quantification measurements of other lipids were conducted. The relative lipid concentration ratios were all set as 2. For each sample, three detections were performed to minimize random error. The averaged quantification result for each lipid was summarized in Table 1 below.

TABLE 1

Relative quantification of different lipids, ethyl oleate, PA 16:0/18:1, PE 16:0/18:1, CE 18:2. Three detections were performed parallelly for each sample to reduce random error.

| Lipids | Concentration Ratio | Measured Mass Reporter Ratio | Relative Error |
|---|---|---|---|
| Ethyl oleate | 2 | 1.85 | 7.5% |
| PA 16:0/18:1 | 2 | 1.91 | 4.5% |
| PE 16:0/18:1 | 2 | 1.90 | 5.0% |
| CE 18:2 | 2 | 1.98 | 1.0% |

As shown in Table 1, measured mass reporter ratios were 1.85, 1.91, 1.90, and 1.98 for ethyl oleate, PA 16:0/18:1, PE 16:0/18:1, and CE 18:2, respectively. The difference between lipid concentration ratio and mass reporter ratio can be generated from different reaction efficiency with distinct concentrations of substrates in the reaction mixture. The instant example provides accurate relative quantification results for lipids from different categories.

Example 4

Analysis of Lipids from Complicated Biological Samples

The method was also evaluated for analyzing lipids from complicated biological samples, for instance human plasma (which contains many types of lipids). In human plasma, CE lipids are the most abundant lipids, so the instant example was designed for CE lipid identification and quantification in human plasma.

A CE lipid extraction method using isooctane and ethyl acetate was applied. High performance liquid chromatography-mass spectrometry (HPLC-MS) was employed to analyze samples. As shown in FIG. 5A, retention times of CE lipids before reaction, after aziridination, after TMT tagging were displayed.

Eleven unsaturated CE lipids were detected from lipid extract based on the accurate masses acquired from a high resolution mass spectrometer, as shown below in Table 2. Acyl chains are released from CE lipids after MS2, and MS3 was performed to acyl chains in order to obtain diagnostic ions for knowing C═C bond positions in CE lipids.

TABLE 2

List of retention times of CE lipid without derivatization and after aziridination and tagging

| | | $[M + NH_4]^+$ | | $[M + Azi]^+$ | | $[M + TMT]^+$ | |
|---|---|---|---|---|---|---|---|
| CE lipid | C=C locations | R.T. (min) | m/z | R.T. (min) | m/z | R.T. (min) | ratio |
| CE 16:1 | Δ7/Δ9 | 16.48 | 640.5963 | 13.83/14.40 | 638.5876 | 14.02 | 2.21 |
| CE 18:1 | Δ9/Δ11 | 16.96 | 668.6276 | 12.90-13.20 | 666.6180 | 14.54 | 1.93 |
| CE 18:2 | Δ9, Δ11/Δ9, Δ12 | 16.50/16.58 | 666.6118 | 13.28/13.39 | 664.6022 | 13.95 | 2.11 |
| CE 20:2 | Δ11, Δ14 | 16.43-17.09 | 694.6439 | 13.39 | 692.6367 | 15.25 | 1.86 |
| CE 20:3 | Δ8, Δ11, Δ14/Δ5, Δ8, Δ11 | 16.53/16.61 | 692.6265 | 13.28 | 690.6148 | 15.10 | 1.98 |
| CE 20:4 | Δ5, Δ8, Δ11, Δ14 | 16.22 | 690.6112 | 13.28 | 688.6022 | 14.02 | 1.03 |
| CE 20:5 | Δ5, Δ8, Δ11, Δ14, Δ17 | 15.90 | 688.5954 | 13.52/13.69 | 686.5860 | 10.51 | 2.10 |
| CE 22:4 | Δ7, Δ10, Δ13, Δ16 | 16.10-16.45 | 718.6431 | 14.08 | 716.6210 | 14.31 | 1.89 |
| CE 22:5 | Δ7, Δ10, Δ13, Δ16, Δ19 | 16.27/16.32 | 716.6264 | 13.83 | 714.5989 | 14.31 | 2.05 |

In FIG. 5A, two peaks are shown in the extracted ion chromatogram (EIC) of CE 18:2 before reaction and after aziridination, which indicate two CE 18:2 lipid isomers exist in our sample. At a retention time of 13.13 minutes, five diagnostic ions at m/z 114, 140, 150, 180, 198 were detected and the lipid was determined to be CE 18:2 (see FIG. 5B).

At a retention time of 13.73 minutes, diagnostic ions at m/z 100, 140, 154, 194, 212 are seen and CE 18:2 was identified (see FIG. 5C). Similarly, based on tandem MS spectra and human metabolome database (HMDB), at least 14 CE lipid isomers have been identified from human plasma. (See FIGS. 6A-6H).

In the EIC of CE 18:2 TMT tagging product, two peaks were not separated, perhaps due to the retention time difference decreased after tagging. Lipid aziridine reaction mixture in the ratio of 1:2 was prepared in separated bottles, and then 100 equivalence of TMT was followed to be added to the aziridine reaction mixture for lipid relative quantification. Ideally, mass reporter ratios of 2 should be achieved for different CE lipids after HCD fragmentation. A typical tandem mass spectrum for tagged CE 18:2 is shown in FIG. 5D, and ratio of mass reporter m/z 126 and 127 is 2.07, which revealed mass reporter ratios can represent lipid ratios in different samples. In FIG. 5E, mass reporter ratio values for different CE lipids are distributed around theoretical ratio 2, which means quantification was successfully demonstrated for complicated sample analyses.

Example 5

Exemplary Reaction Schemes for Novel Mass Tags

The instant example provides exemplary reaction schemes that can be utilized for synthesis of the mass tags described in the present disclosure.

Exemplary Reactions for Group I Mass Tags

Figure 6:
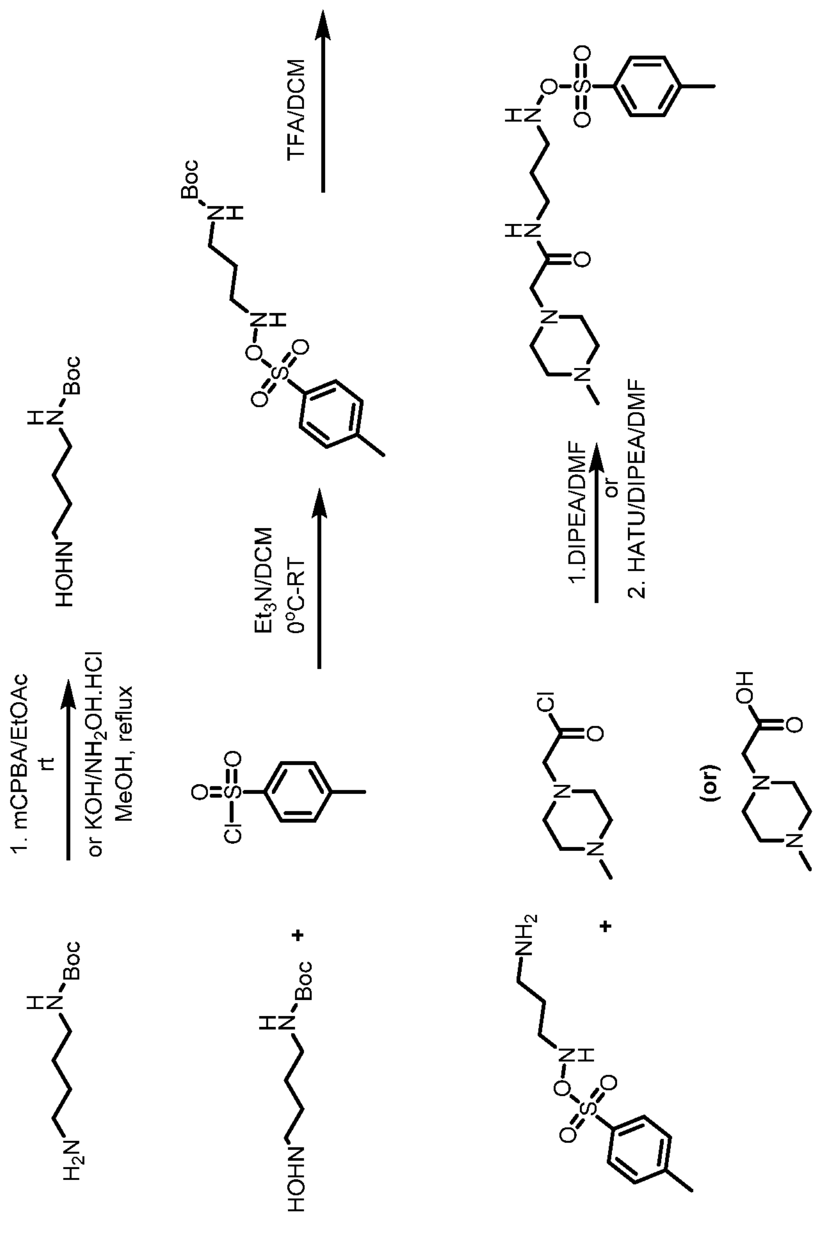
FIG. 6 shows a representative synthetic route for Group I mass tags.
Figure 7:
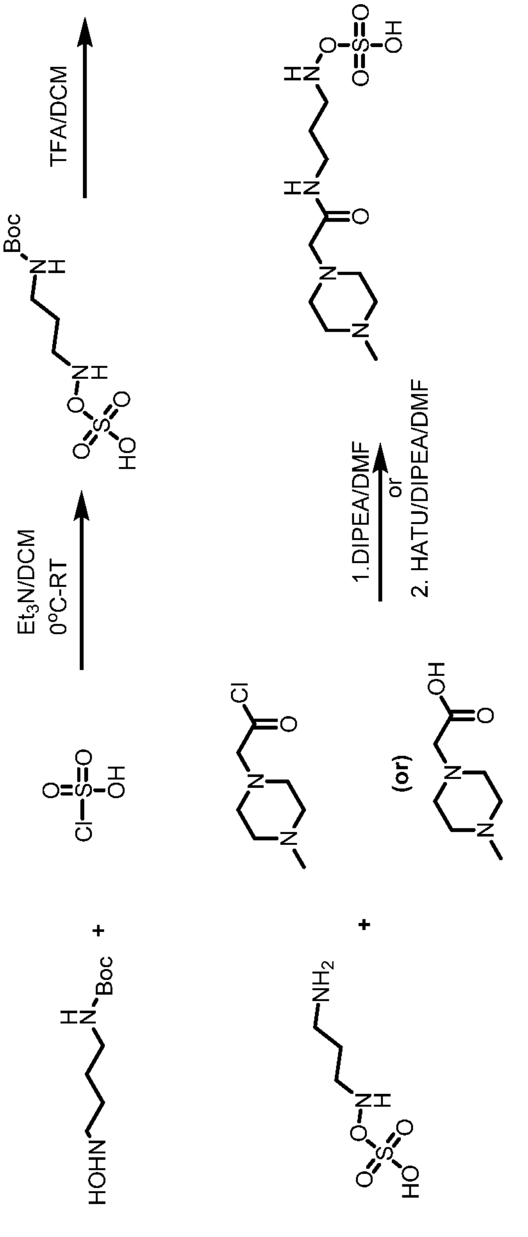
FIG. 7 shows a representative synthetic route for Group I mass tags.

In an embodiment, a representative synthetic route for Group I mass tags comprises the scheme presented in FIG. 6. In an embodiment, a representative synthetic route for Group I mass tags comprises the scheme presented in FIG. 7.

Exemplary Reactions for Group II Mass Tags

Figure 8:
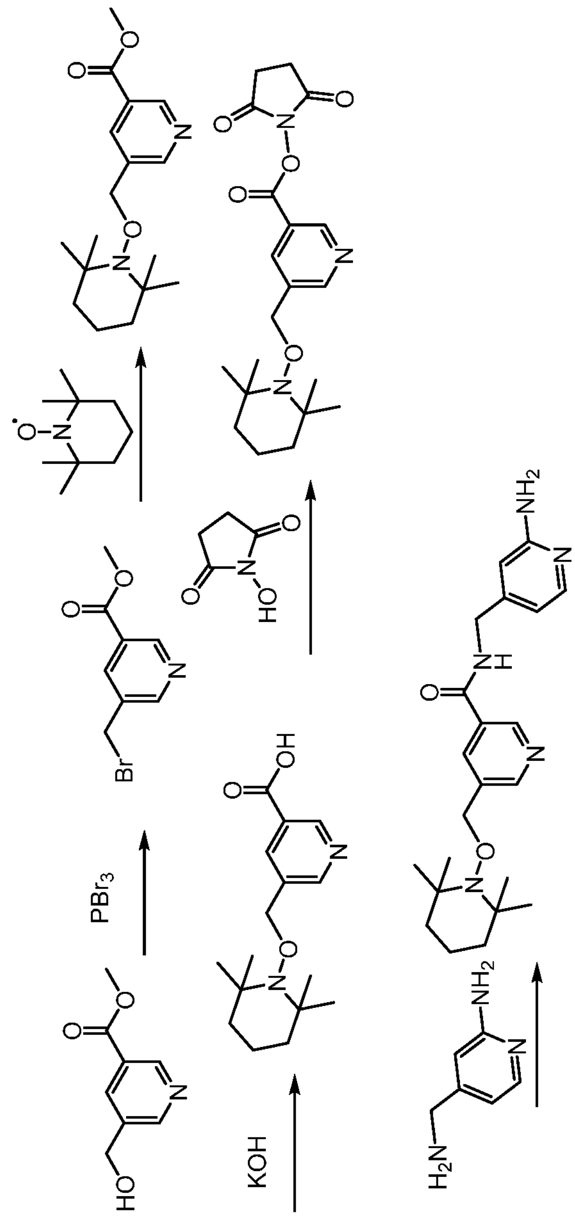
FIG. 8 shows a representative synthetic route for Group II mass tags.

In an embodiment, a representative synthetic route for Group II mass tags comprises the scheme presented in FIG. 8.

Exemplary Reactions for Group III Mass Tags

Figure 9:
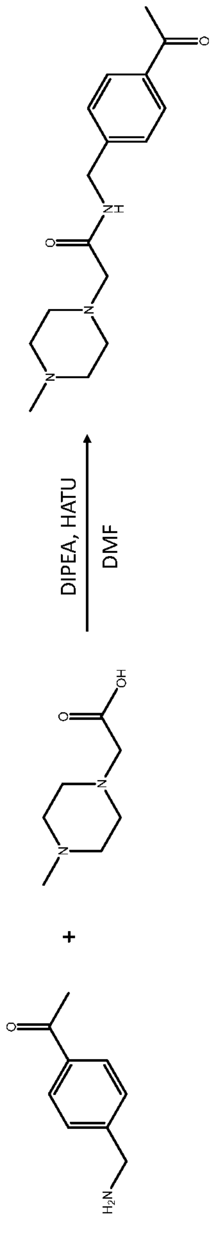
FIG. 9 shows a representative synthetic route for Group III mass tags.
Figure 10:
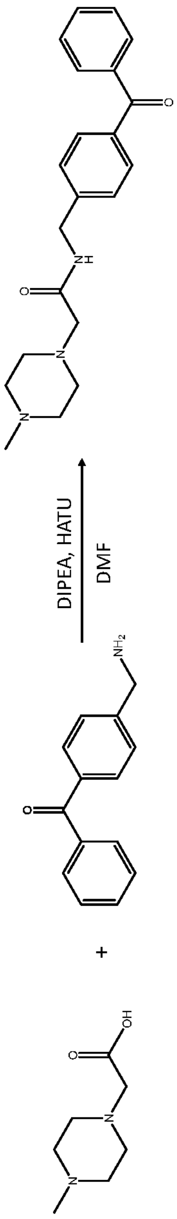
FIG. 10 shows a representative synthetic route for Group III mass tags.
Figure 11:
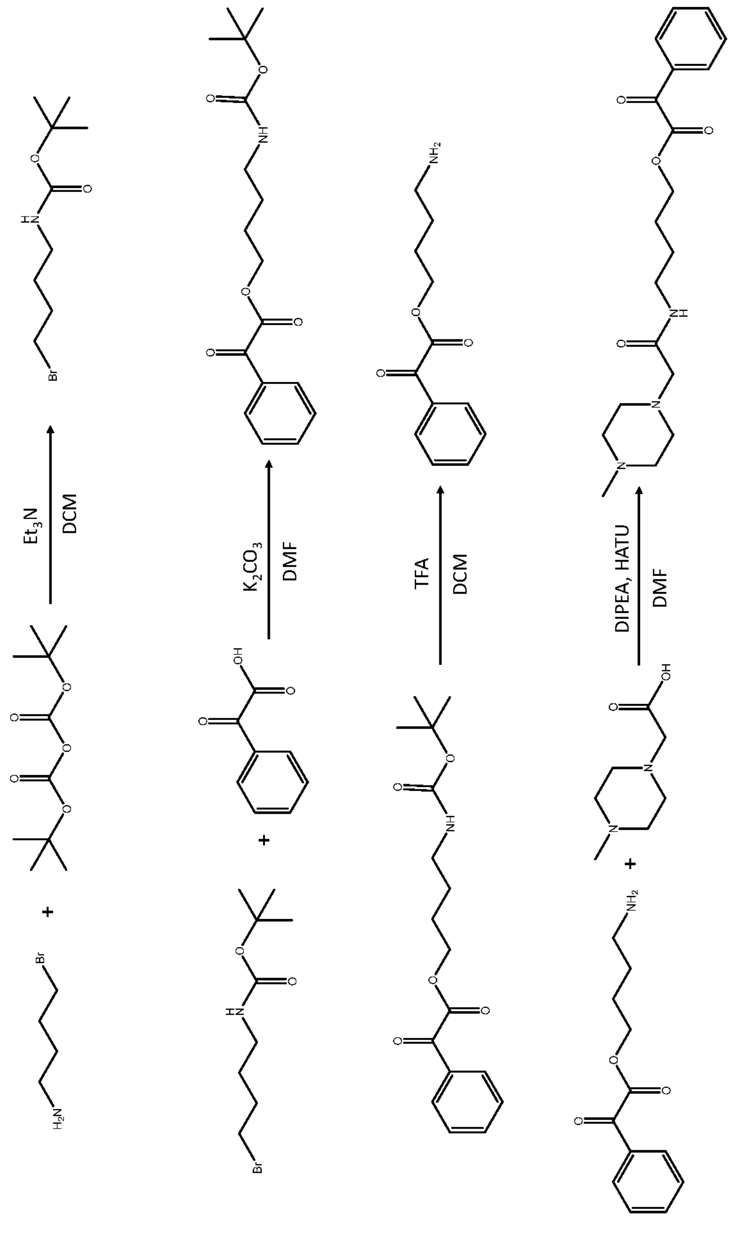
FIG. 11 shows a representative synthetic route for Group III mass tags.

In an embodiment, a representative synthetic route for Group III mass tags comprises the scheme presented in FIG. 9. In an embodiment, a representative synthetic route for Group III mass tags comprises the scheme presented in FIG. 10. In an embodiment, a representative synthetic route for Group III mass tags comprises the scheme presented in FIG. 11.

Example 6

Use of Novel Mass Tags for Lipid Identification and Quantification

The novel mass tags of the present disclosure can be utilized in the described methods herein. For instance, the novel mass tags (for example, embodiments of Group I, Group II, and Group III mass tags) can be used in methods of quantifying one or more individual lipids from a composition of lipids as described herein. Further, the novel mass tags can be used in methods of identifying a double bond position of an individual lipid as described herein. Moreover, the novel mass tags can be used in methods of identifying a biological correlation of an individual lipid as described herein. Also, the novel mass tags can be used in methods of preparing a lipid derivative as described herein.

One advantage of using the novel mass tags of the present disclosure according to the instant example is that the novel mass tags can be utilized in a single step to provide an aziridination reaction on a lipid and application of the mass tag to the lipid. Prior to the creation of the novel mass tags, such methods would need to undergo two separate steps (i.e., an aziridination reaction followed by a separate application of a mass tag to the aziridinated lipid). Utilizing the novel mass tags of the present disclosure can provide an efficient and precise methodology in a single step, thus avoiding the need to perform two separate steps.

Figure 12:
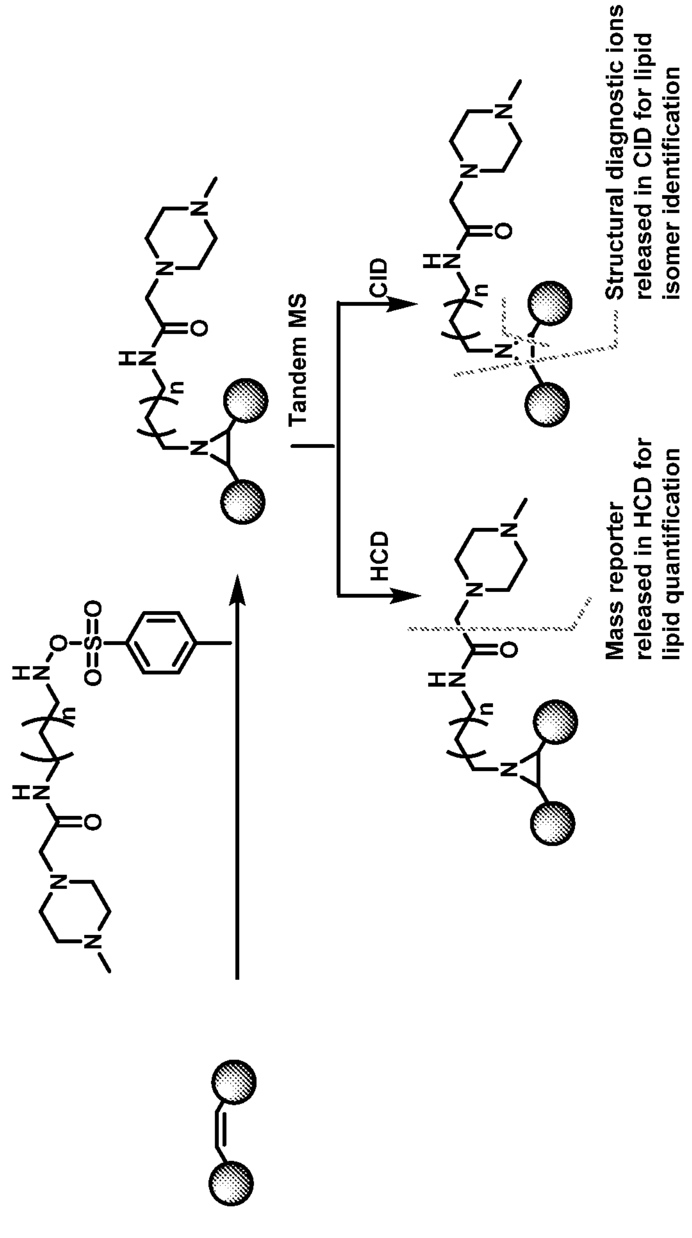
FIG. 12 shows an exemplary utilization of a mass tag according to the Group I mass tags described herein in a method of identifying a double bond position of an individual lipid. HCD refers to "higher energy collision induced dissociation" and CID refers to "collision induced dissociation," referring to two tandem mass spectrometric methods that can be accomplished using a single instrument.

For instance, a mass tag according to the Group I mass tags described herein can be utilized in a method of identifying a double bond position of an individual lipid according to the exemplary scheme shown in FIG. 12.

Figure 13:
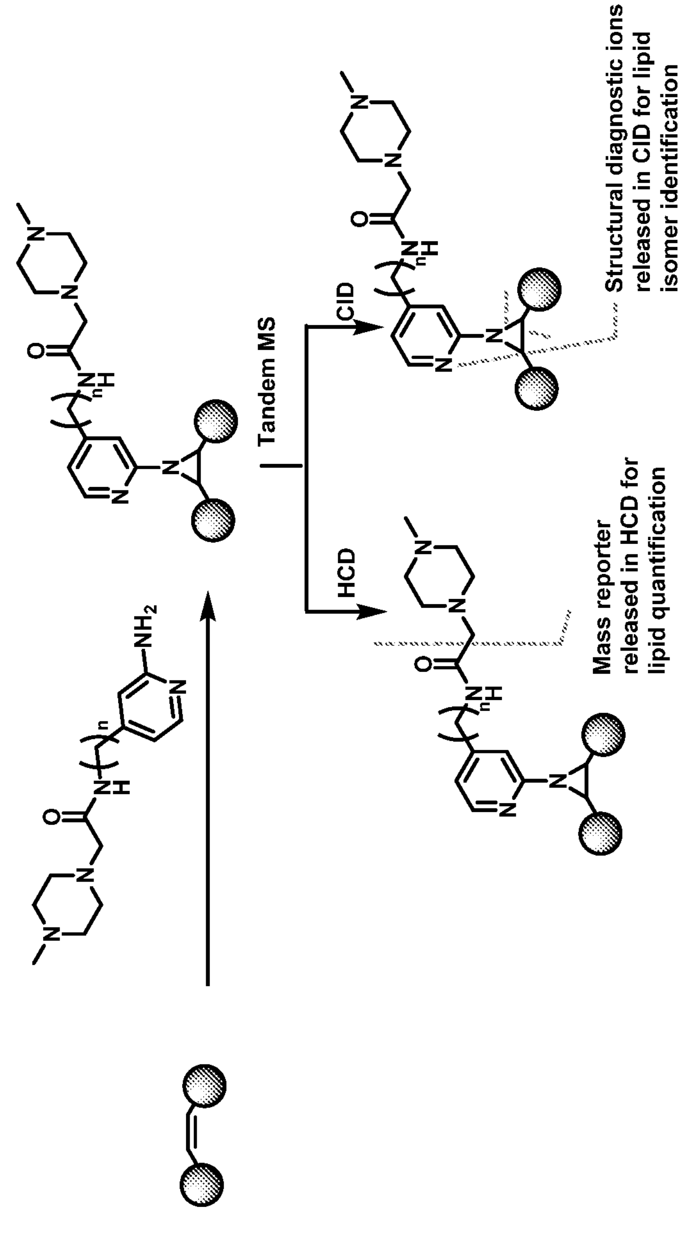
FIG. 13 shows an exemplary utilization of a mass tag according to the Group II mass tags described herein in a method of identifying a double bond position of an individual lipid.

For instance, a mass tag according to the Group II mass tags described herein can be utilized in a method of identifying a double bond position of an individual lipid according to the exemplary scheme shown in FIG. 13.

Figure 14:
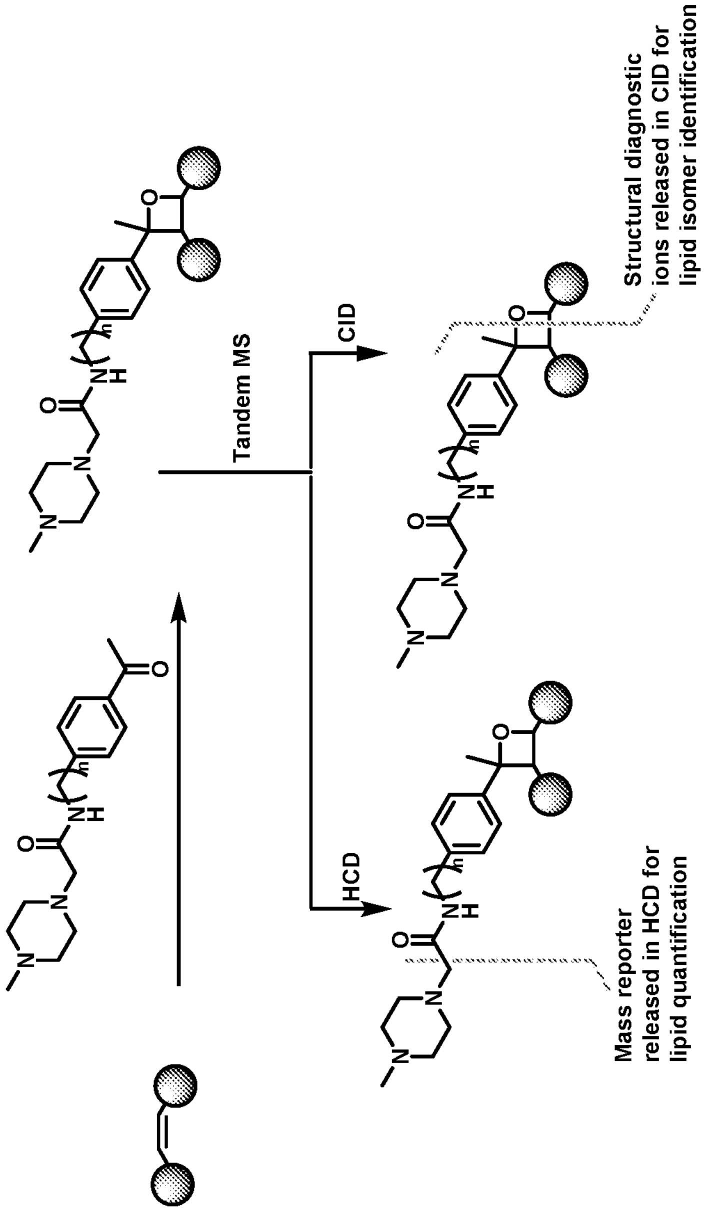
FIG. 14 shows an exemplary utilization of a mass tag according to the Group III mass tags described herein in a method of identifying a double bond position of an individual lipid.

For instance, a mass tag according to the Group III mass tags described herein can be utilized in a method of identifying a double bond position of an individual lipid according to the exemplary scheme shown in FIG. 14.

Example 7

Use of Novel Mass Tags for Identification of Biological Correlations of Individual Lipids The novel mass tags of the present disclosure can be utilized in the described methods herein. For instance, the novel mass tags (for example, embodiments of Group I, Group II, and Group III mass tags) can be used in methods of identifying a biological correlation of an individual lipid. One advantage of using the novel mass tags of the present disclosure according to the instant example is that the novel mass tags can be utilized in a single step to provide an aziridination reaction on a lipid and application of the mass tag to the lipid. Prior to the creation of the novel mass tags, such methods would need to undergo two separate steps (i.e., an aziridination reaction followed by a separate application of a mass tag to the aziridinated lipid). Utilizing the novel mass tags of the present disclosure can provide an efficient and precise methodology in a single step, thus avoiding the need to perform two separate steps.

What is claimed is:

1. A composition comprising a mass tag, wherein the mass tag has a structure of

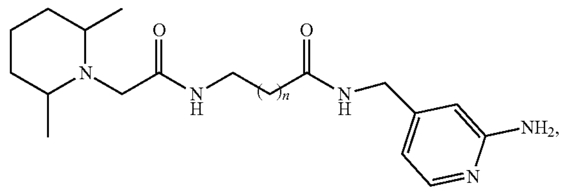

wherein n is between 0 and 10.

2. A composition comprising a mass tag, wherein the mass tag has a structure selected from the group consisting of:

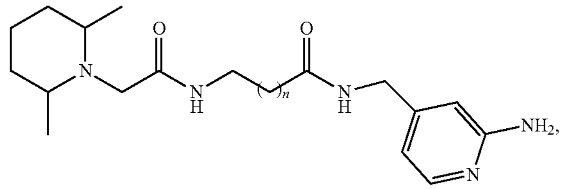

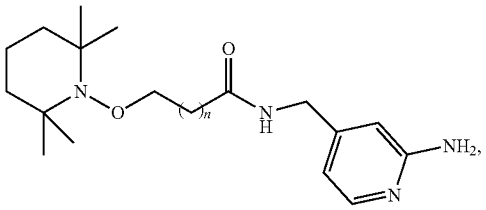

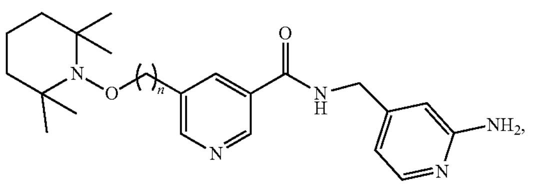

and

-continued

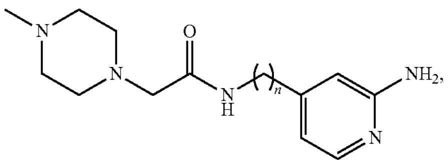

wherein n is between 0 and 10.

3. The composition of claim 2, wherein the mass tag has a structure of

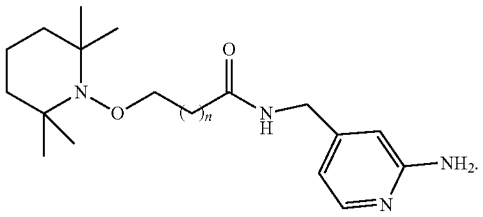

4. The composition of claim 2, wherein the mass tag has a structure of

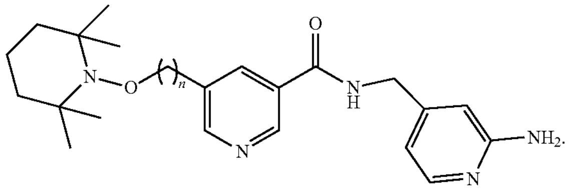

5. The composition of claim 2, wherein the mass tag has a structure of

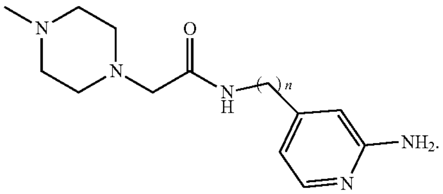

6. A method of quantifying one or more individual lipids from a composition of lipids, said method comprising the steps of:

combining the composition of lipids with one or more mass tags to form a tagged lipid composition, performing mass spectrometry on the tagged lipid composition to identify the one or more individual lipids, and quantifying the one or more individual lipids, wherein the mass tag is present as the composition of claim 2.

7. The method of claim 6, wherein the mass tag has a structure of

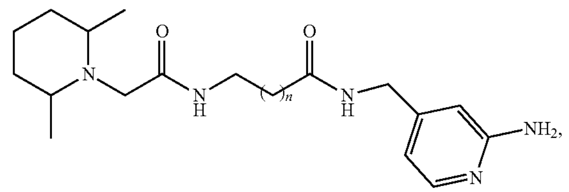

wherein n is between 0 and 10.

8. The method of claim 6, wherein the composition of lipids comprises one or more unsaturated lipids.

9. The method of claim 6, wherein the composition of lipids is blood.

10. The method of claim 6, wherein the composition of lipids is plasma.

11. The method of claim 6, wherein the method does not require a lipid internal standard.

12. The method of claim 6, wherein the mass spectrometry comprises tandem mass spectrometry.

13. The method of claim 6, wherein the method comprises a step of identifying a double bond position of the one or more individual lipids.

14. The method of claim 13, wherein the mass tag has a structure of

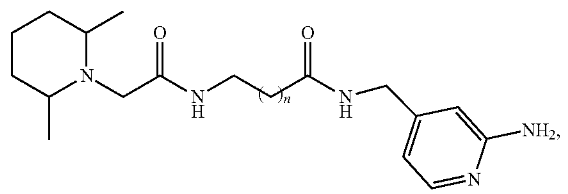

wherein n is between 0 and 10.

15. The method of claim 13, wherein the double bond position is a carbon-carbon double bond position.

16. The method of claim 13, wherein the composition of lipids comprises one or more unsaturated lipids.

17. The method of claim 13, wherein the composition of lipids is blood or plasma.

18. The method of claim 13, wherein the method does not require a lipid internal standard.

19. The method of claim 13, wherein the mass spectrometry comprises tandem mass spectrometry.

* * * * *